(12) United States Patent
Rehder et al.

(10) Patent No.: US 7,705,132 B2
(45) Date of Patent: Apr. 27, 2010

(54) STABLE POLYPEPTIDE FORMULATIONS

(75) Inventors: Douglas Rehder, Seattle, WA (US); Pavel Bondarenko, Thousand Oaks, CA (US); Dirk Chelius, Geretsried (DE); Arnold McAuley, Moorpark, CA (US); Masazumi Matsumura, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 27 days.

(21) Appl. No.: 11/973,051

(22) Filed: Oct. 5, 2007

(65) Prior Publication Data

US 2008/0124326 A1 May 29, 2008

Related U.S. Application Data

(60) Provisional application No. 60/853,181, filed on Oct. 20, 2006.

(51) Int. Cl.
*C07K 16/00* (2006.01)
*C12P 21/08* (2006.01)
*A61K 39/00* (2006.01)
*A61K 39/395* (2006.01)

(52) U.S. Cl. ............ 530/387.1; 530/387.3; 530/388.15; 530/388.22; 424/133.1; 424/143.1

(58) Field of Classification Search ........................ None
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant, Jr. et al. | |
| 4,447,233 A | 5/1984 | Mayfield | |
| 4,475,196 A | 10/1984 | La Zor | |
| 4,475,916 A | 10/1984 | Himmelstein | |
| 4,486,194 A | 12/1984 | Ferrara | |
| 4,487,603 A | 12/1984 | Harris | |
| 4,522,811 A | 6/1985 | Eppstein et al. | |
| 4,596,556 A | 6/1986 | Morrow et al. | |
| 4,597,966 A | 7/1986 | Zolton et al. | |
| 4,790,824 A | 12/1988 | Morrow et al. | |
| 4,941,880 A | 7/1990 | Burn | |
| 5,064,413 A | 11/1991 | McKinnon et al. | |
| 5,237,054 A | 8/1993 | Brinks et al. | |
| 5,312,335 A | 5/1994 | McKinnon et al. | |
| 5,374,548 A | 12/1994 | Caras | |
| 5,383,851 A | 1/1995 | McKinnon, Jr. et al. | |
| 5,399,163 A | 3/1995 | Peterson et al. | |
| 5,399,331 A | 3/1995 | Loughrey et al. | |
| 5,416,016 A | 5/1995 | Low et al. | |
| 5,427,908 A | 6/1995 | Dower et al. | |
| 5,654,403 A | 8/1997 | Smith et al. | |
| 5,714,350 A | 2/1998 | Co et al. | |
| 5,792,838 A | 8/1998 | Smith et al. | |
| 5,877,293 A | 3/1999 | Adair et al. | |
| 5,886,152 A | 3/1999 | Nakatani et al. | |
| 5,891,873 A | 4/1999 | Colaco et al. | |
| 5,908,826 A | 6/1999 | Fukuda et al. | |
| 5,955,448 A | 9/1999 | Colaco et al. | |
| 6,034,080 A | 3/2000 | Colaco et al. | |
| 6,054,297 A | 4/2000 | Carter et al. | |
| 6,171,586 B1 | 1/2001 | Lam et al. | |
| 6,235,883 B1 | 5/2001 | Jakobovits et al. | |
| 6,267,958 B1 | 7/2001 | Andya et al. | |
| 6,313,102 B1 | 11/2001 | Colaco et al. | |
| 7,060,808 B1 | 6/2006 | Goldstein et al. | |
| 2003/0091561 A1 | 5/2003 | van de Winkel et al. | |
| 2003/0113316 A1 | 6/2003 | Kaisheva et al. | |
| 2003/0138417 A1 | 7/2003 | Kaisheva et al. | |
| 2003/0194403 A1 | 10/2003 | van de Winkel et al. | |
| 2004/0009168 A1 | 1/2004 | Kaisheva et al. | |
| 2004/0033228 A1 | 2/2004 | Krause et al. | |
| 2004/0038878 A1 | 2/2004 | Tanikawa et al. | |
| 2004/0191243 A1 | 9/2004 | Chen et al. | |
| 2005/0053598 A1 | 3/2005 | Burke et al. | |
| 2005/0175611 A1* | 8/2005 | Mahler et al. ............ 424/145.1 |
| 2006/0194280 A1 | 8/2006 | Dillon et al. | |
| 2007/0087394 A1 | 4/2007 | Siena et al. | |

FOREIGN PATENT DOCUMENTS

EP 0392717 10/1990

(Continued)

OTHER PUBLICATIONS

Al-Lazikani et al., "Standard Conformations for the Canonical Structures of Immunoglobulins", J. Mol. Biol., 273:927-948 (1997).
Barbas et al., "Assembly of Combinatorial Antibody Libraries on Phage Surfaces: The gene III site", Proc. Natl. Acad. Sci. USA, 88:7978-7982 (1991).
Bird et al., "Single-Chain Antigen-Binding Proteins", Science, 242:423-426(1988).
Bloeman et al., "Adhesion Molecules: A New Target for Immunoliposome-mediated Drug Delivery", FEBS Lett., 357:140-144 (1995).
Brange et al., Chemical Stability of Insulin. 3. Influence of Excipients, Formulation and pH, Acta Pharm Nordica, 4:149-158 (1992).
Chothia et al., "Canonical Structures for the Hypervariable Regions of Immunoglobulins", J. Mol. Biol., 196:901-917 (1987).
Felici et al., "Selection of Antibody Ligands from a Large Library of Oligopeptides Expressed on a Multivalent Exposition Vector", J. Mol. Biol., 222:301-310 (1991).
Hammerling et al., "Production of Antibody-Producing Hybridomas in the Rodent Systems", Monoclonal Antibodies and T-Cell Hybridomas, 563-681, Elsevier, N.Y. (1981).

(Continued)

*Primary Examiner*—Robert Landsman
(74) *Attorney, Agent, or Firm*—Scott N. Bernstein

(57) ABSTRACT

The invention provides a formulation including a buffer having a pH less than 6.0, a divalent cation between about 5-200 mM, an excipient comprising a sugar or polyol and an effective amount of a therapeutic polypeptide. Also provided is a method of stabilizing a polypeptide. The method includes contacting a therapeutic polypeptide with a concentration of divalent cation between about 5-150 150 mM in a buffer having a pH less than 6.0 and an excipient comprising a sugar or polyol.

22 Claims, 18 Drawing Sheets

FOREIGN PATENT DOCUMENTS

| | | |
|---|---|---|
| EP | 0988861 | 3/2000 |
| EP | 1254666 | 11/2002 |
| EP | 1391209 | 2/2004 |
| WO | WO 96/05809 | 2/1996 |
| WO | WO 98/42376 | 10/1998 |
| WO | WO 00/62759 | 10/2000 |
| WO | WO 02/30463 | 4/2002 |
| WO | WO 02/38170 | 5/2002 |
| WO | WO 02/068455 | 9/2002 |
| WO | WO 02/096457 | 12/2002 |
| WO | WO 03/039485 | 5/2003 |
| WO | WO 03/066660 | 8/2003 |
| WO | WO 03/106644 | 12/2003 |
| WO | WO 2004/004639 | 1/2004 |
| WO | WO 2004/039337 | 5/2004 |
| WO | WO 2004/039826 | 5/2004 |
| WO | WO 2004/066957 | 8/2004 |
| WO | WO 2004/071439 | 8/2004 |
| WO | WO 2006/096461 | 9/2006 |
| WO | WO2006/107854 A2 | 10/2006 |
| WO | WO 2007/145862 | 12/2007 |
| WO | WO2007/147001 * | 12/2007 |

OTHER PUBLICATIONS

Hesmeling et al., "Structural Characterization and Immunogenicity in Wild-Type and Immune Tolerant Mice of Degraded Recombinant Human Interferon Alpha2b", Pharm. Res., 22(12):1997-2006 (2005).

Holliger et al., ""Diabodies": Small Bivalent And Bispecific Antibody Fragments", Proc. Natl. Acad. Sci. USA, 90:6444-6448 (1993).

Huse et al., Generation of a Large Combinatorial Library of the Immunoglobulin Repertoire in Phage Lambda, Science, 246:1275-1281 (1989).

Huse, W., "Combinatorial Antibody Expression Libraries in Filamentous Phage", Antibody Engineering: A Practical Guide, C.A.K. Borrebaeck, Ed., W.H. Freeman and Co., Publishers, New York, pp. 103-120 (1991).

Huston et al., "Antigen Recognition and Targeted Delivery by the Single-Chain Fv", Cell Biophysics, 22:189-224 (1993).

Huston et al., "Protein Engineering of Antibody Binding Sites: Recovery of Specific Activity in an Anti-digoxin Single-chain Fv Analogue Produced in *Escherichia coli*", Proc. Natl. Acad. Sci. USA, 85:5879-5883 (1988).

Kabat et al., "Unusual Distributions of Amino Acids in Complementarity-determining (Hypervariable) Segments of Heavy and Light Chains of Immunoglobulins and Their Possible Roles in Specificity of Antibody-combining Sites", J. Biol. Chem., 252(19):6609-6616 (1977).

Kabat, E. "The Structural Basis of Antibody Complementarily", Adv. Prot. Chem., 32:1-75 (1978).

Kang et al., "Linkage of Recognition and Replication Functions by Assembling Combinatorial Antibody Fab Libraries Along Phage Surfaces", Proc. Natl. Acad. Sci. USA, 88:4363-4366 (1991).

Lerner et al., "Antibodies Without Immunization", Science, 258:1313-1314 (1992).

Mendelsohn et al., "Status of Epidermal Growth Factor Receptor Antagonists in the Biology and Treatment of Cancer", J. Clin. Oncol., 21(14):2787-2799 (2003).

Morea et al., "Antibody Modeling: Implications for Engineering and Design", Methods, 20:267-279 (2000).

Owais et al., "Chloroquine Encapsulated in Malaria-Infected Erythrocyte-Specific Antibody-Bearing Liposomes Effectively Controls Chloroquine-Resistant *Plasmodium berghei* Infections in Mice", Antimicrob. Agents Chemother., 39(1):180-184 (1995).

Peek et al., A Rapid, Three-step Process for the Preformulation of a Recombinant Richin Toxin A-chain Vaccine, Journal of Pharm Sci, 96:44-60 (2007).

Pourrat et al., "Stabilization of Octastatin, a Somatostatin Analogue. Preparation of Freeze-dried Products for Parenteral Injection", Biological and Pharm Bulletin, 18:766-771 (1995).

Plückthun et al., "Expression of Functional Antibody Fv and Fab Fragments in *Escherichia coli*", Meth. Enzymol, 178:497-515 (1989).

Poljak et al., "Production and Structure of Diabodies", Structure, 2:1121-1123 (1994).

Quinn et al., "Minimizing the Aggregation of Neutral Insulin Solutions", Journal of Pharm. Sci., 72:1472-1473 (1983).

Ranade, V., "Drug Delivery Systems. 1. Site-Specific Drug Delivery Using Liposomes as Carriers", J. Clin. Pharmacol., 29:685-694 (1989).

Randolph et al., "Surfactant-Protein Interactions", Pharm Biotechnol., 13:159-175 (2002).

Schellekens, H., "Bioequivalence and the Immunogenicity of Biopharmaceuticals", Nat. Rev. Drug Discov. 1:457-462 (2002).

Tang et al., The Effect of Stabilizers and Denaturants on the Cold Denaturation Temperatures of Proteins and Implications for Freeze-drying, Pharmaceutical Research, 22:1167-1175 (2005).

Umezawa et al., "Liposome Targeting to Mouse Brain: Mannose as a Recognition Marker", Biochem,. Biophys. Res. Commun., 153(3):1038-1044 (1988).

Wakankar et al, "The Effect of Consolutes on the Isomerization of Aspartic Acid Residues and Conformational Stability in a Monoclonal Antibody", Journal of Pharmaceutical Sciences, 96:1708-1718 (2007).

Wang, W., "Instability, Stabilization, and Formulation of Liquid Protein Pharmaceuticals", Int. J. Pharm., 185:129-188 (1999).

Wang, W., Lyophilization and Development of Solid Protein Pharmaceuticals, Int. J. Pharm., 203:1-60 (2000).

Ward et al,"Binding Activities of a Repertoire of Single Immunoglobulin Variable Domains Secreted from *Escherichia coli*", Nature 341:544-546 (1989).

Yarden et al., "Untangling the ErbB Signaling Network", Nat. Rev. Mol. Cell. Biol., 2:127-137 (2001).

* cited by examiner

ABX-EGF HIAC
LOT 8 PF690 4C T= 1yr
≥10um

PF1002 Frozen Study -30C

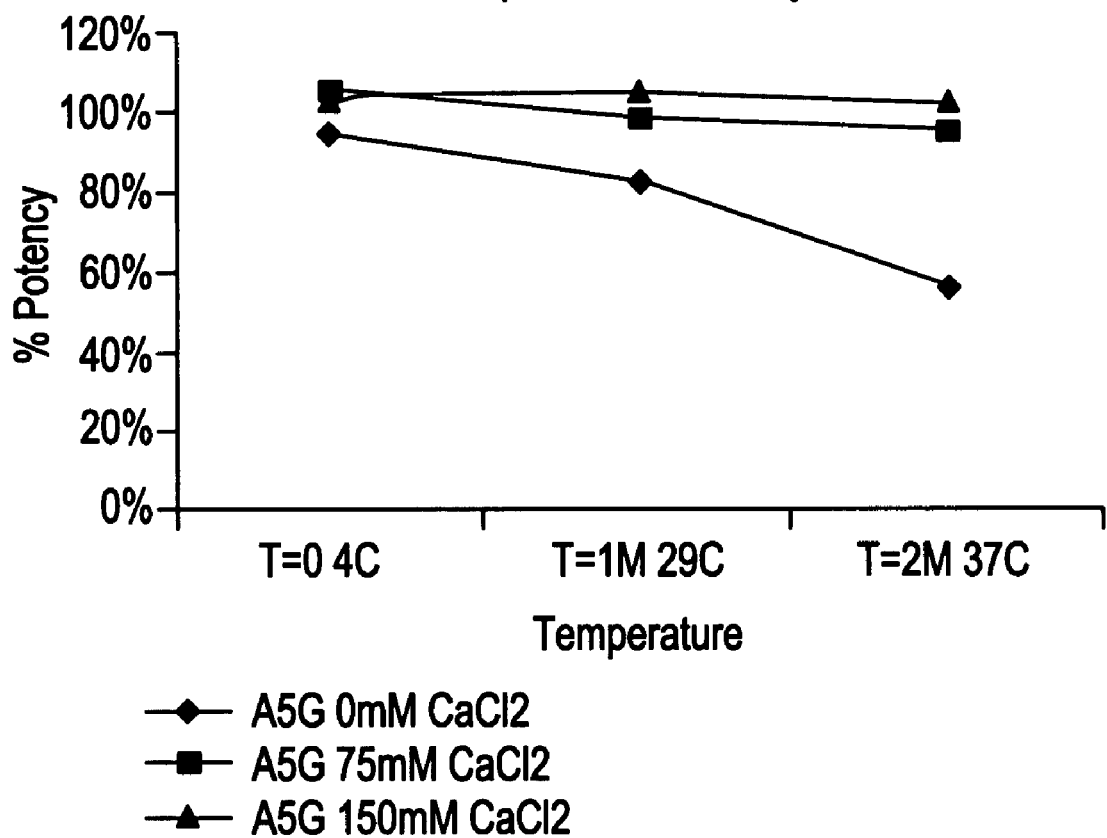

STABLE POLYPEPTIDE FORMULATIONS

This application is based on, and claims the benefit of, U.S. Provisional Application Ser. No. 60/853,181, filed Oct. 20, 2006, which is expressly incorporated herein by reference in its entirety.

BACKGROUND OF THE INVENTION

This invention relates generally to medicines for the treatment of diseases and, more specifically to consistently stable formulations for polypeptide therapeutics.

With the advent of recombinant DNA technology, protein-based therapeutics have become continually and increasingly commonplace in the repertoire of drugs available to medical practitioners for the treatment of a wide range of diseases from cancer to autoimmune diseases. Along with the scientific and technical advances that have occurred in the production of recombinant proteins, another reason for the success of protein therapeutics is their high specificity towards targets and their ability to exhibit superior safety profiles when compared to small molecule therapeutics. The ability to employ biological molecules as pharmaceuticals in the treatment of diseases has significantly advanced medical care and quality of life over the past quarter of a century.

Proteins known to exhibit various pharmacological actions in vivo are now capable of being produced in large amounts for various pharmaceutical applications. Long-term stability of a therapeutic protein is a particularly beneficial criterion for safe, consistent and efficacious treatments. Loss of functionality of the therapeutic within a preparation will decrease its effective concentration for a given administration. Similarly, undesired modifications of a therapeutic can affect the activity and/or the safety of a preparation, leading to loss of efficacy and risk of adverse side effects.

Proteins are complex molecules with defined primary, secondary, tertiary and in some cases quaternary structures, all of which play a role in imparting specific biological function. Structural complexity of biological pharmaceuticals such as proteins make them susceptible to various processes that result in structural and functional instability as well as loss of safety. With respect to these instability processes or degradation pathways, a protein can undergo a variety of covalent and non-covalent reactions or modifications in solution. For example, protein degradation pathways can be generally classified into two main categories: (i) physical degradation or non-covalent pathways, and (ii) chemical or covalent degradation pathways.

Protein drugs are susceptible to the physical degradation process of irreversible aggregation. Protein aggregation is of particular interest in polypeptide production because it often results in diminished bioactivity that affects drug potency, and also can elicit serious immunological or antigenic reactions in patients. Chemical degradation of a protein therapeutic, including degradation of the chemical structure by, for example, chemical modification, also has been implicated in increasing its immunogenic potential. Thus, stable protein formulations require that both physical and chemical degradation pathways of the drug be minimized.

Proteins can degrade, for example, via physical processes such as interfacial adsorption and aggregation. Adsorption can significantly impact a protein drug's potency and stability. It can cause an appreciable loss in potency of low concentration dosage forms. A second consequence is that unfolding mediated adsorption at interfaces can often be an initiating step for irreversible aggregation in solution. In this respect, proteins tend to adsorb at liquid-solid, liquid-air, and liquid-liquid interfaces. Sufficient exposure of a protein's core at a hydrophobic surface can result in adsorption as a consequence of agitation, temperature or pH induced stresses. Further, proteins also are sensitive to, for example, pH, ionic strength, thermal stress, shear and interfacial stresses, all of which can lead to aggregation and result in instability. Another consequence of aggregation is particle formation an important consideration in liquid and lyophilized protein pharmaceuticals.

Proteins also are subject to a variety of chemical modification and/or degradation reactions such as deamidation, isomerization, hydrolysis, disulfide scrambling, beta-elimination, oxidation and adduct formation. The principal hydrolytic mechanisms of degradation include peptide bond hydrolysis, deamidation of asparagine and glutamine, isomerization of aspartic acid and cyclization of glutamic acid leading to pyro-glutamic acid. A common feature of the hydrolytic degradation pathways is that one significant formulation variable, with respect to the rates of the reactions, is the solution pH.

For example, the hydrolysis of peptide bonds can be acid or base catalyzed. Asparagine and glutamine deamidation also are acid catalyzed below a pH of about 4. Asparagine deamidation at neutral pH occurs through a succinimidyl intermediate that is base catalyzed. The isomerization and racemization of aspartic acid residues can be rapid in slightly acidic to neutral pH (pH 4-8). In addition to the generalized pH effects, buffer salts and other excipients can affect the rates of the hydrolytic reactions.

Other exemplary degradation pathways include beta-elimination reactions, which can occur under alkaline pH conditions and lead to racemization or loss of part of the side-chain for certain amino acids. Oxidations of methionine, cysteine, histidine, tyrosine and tryptophan residues are exemplary covalent degradation pathways for proteins.

Because of the number and diversity of different reactions that can result in protein instability the composition of components in a formulation can significantly affect the extent of protein degradation and, consequently, the safety and efficacy of the therapeutic. The formulation of a polypeptide also can affect the ease and frequency of administration and pain upon injection. For example, immunogenic reactions have not only been attributed to protein aggregates but also to mixed aggregates of the therapeutic protein with an inactive component contained in the formulation (Schellekens, H., Nat. Rev. Drug Discov. 1:457-62(2002); Hesmeling, et al., Pharm. Res. 22:1997-2006 (2005)).

However, despite the advances made in the utilization of proteins in therapeutic treatments and the knowledge of the instability process they can undergo, there is still a need to develop formulations with enhanced long-term stability characteristics. A formulation that retains long-term stability under a variety of conditions would provide an effective means of delivering an efficacious and safe amount of the polypeptide. Retention of long-term stability in a formulation also would lower the production and treatment costs. Numerous recombinant or natural proteins could benefit from such consistently stable formulations and thereby provide more effective clinical results.

Thus, there exists a need for formulations that retain long-term stability under a variety of different manufacturing and storage conditions. The present invention satisfies this need and provides related advantages as well.

SUMMARY OF THE INVENTION

The invention provides a formulation including a buffer having a pH less than 6.0, a divalent cation between about 5-200 mM, an excipient comprising a sugar or polyol and an effective amount of a therapeutic polypeptide. Also provided is a method of stabilizing a polypeptide. The method includes contacting a therapeutic polypeptide with a concentration of divalent cation between about 5-150 150 mM in a buffer having a pH less than 6.0 and an excipient comprising a sugar or polyol.

BRIEF DESCRIPTION OF THE DRAWINGS

(FIG. 16A), 29° C. (FIG. 16B) and at 37° C. (FIG. 16C) in solutions with different concentrations of calcium chloride ($CaCl_2$) at pH 5.0. The histogram sets for each time period correspond from left to right to A5G, A5G25CA, A5G50CA, A5G75CA, A5G100CA, and A5G150CA.

FIG. 17 shows the effects of $CaCl_2$ on antibody potency loss using cell proliferation assay measurements of antibody potency with varying concentrations of $CaCl_2$.

FIG. 18 shows the SE-HPLC profile of an antibody formulated in 0-150 mM $Cacl_2$ following storage for 4 months at 4° C.

DETAILED DESCRIPTION OF THE INVENTION

Figure 1:
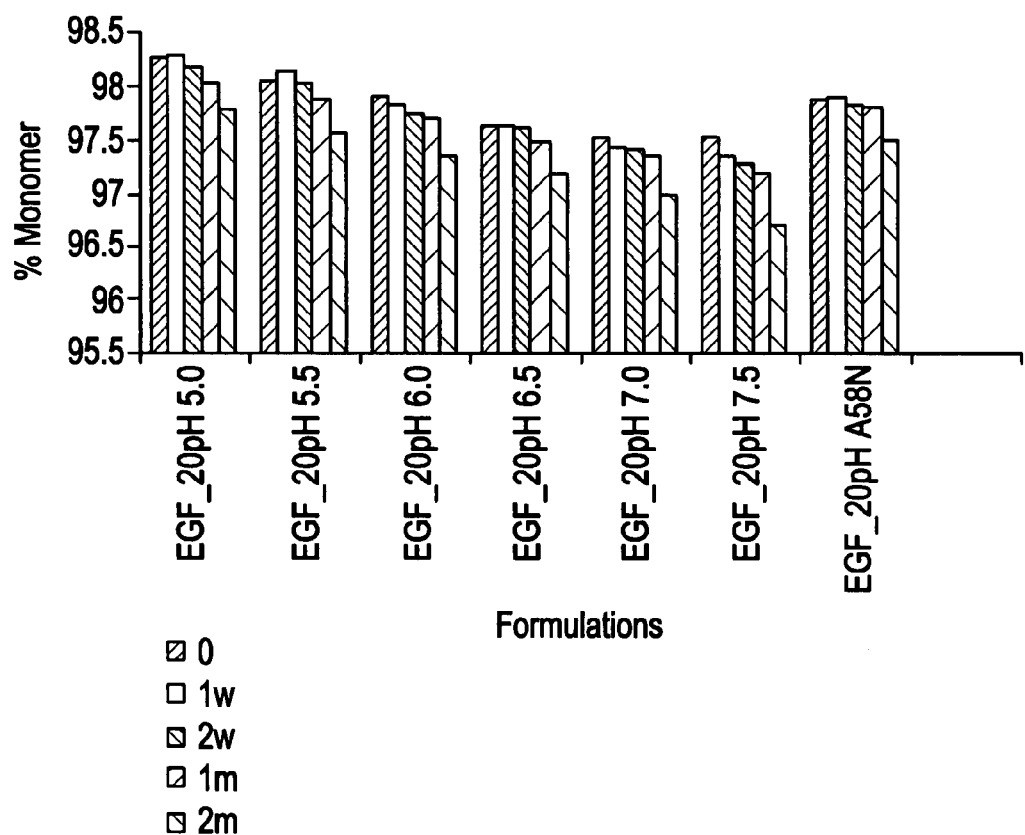
FIG. 1 shows SE-HPLC results for the pH stability of an antibody formulation stored at 37° C. for up to 2 months. Histogram sets for each measured pH correspond from left to right to storage periods of no storage (0); 1 week (1 w); 2 weeks (2 w); 1 month (1 m), and 2 months (2 m). For each time point, the pH values corresponded to 5.0, 5.5, 6.0, 6.5, 7.0 and 7.5.

The invention is directed to a formulation that can stabilize aqueous and other liquid polypeptide solutions as well as lyophilized formulations. The formulation of the invention is useful with polypeptides susceptible to aspartic acid (Asp or D) or asparagine (Asn or N) isomerization because it prevents or reduces the rate or extend of isoaspartic acid formation. Susceptible polypeptides include those having solvent-exposed Asp or Asn because they tend to form succinimide intermediates via hydrolysis or deamination reactions promoted by solvent and form destabilizing isoaspartyl residues. Reduction in the rate or extent of isoaspartic acid formation is accomplished by inclusion of one or more divalent cations, or a salt form thereof, together with the polypeptide and/or other formulation components.

In a specific embodiment of the invention, the polypeptides stabilized by a formulation of the invention are antibodies that contain solvent-exposed aspartic acid or asparagine. In this specific embodiment, the hydrolysis or deamination reaction kinetics can be slowed down with the addition of between about 10-150 mM $CaCl_2$. Such antibodies include those having Asp or Asn residues in one or more CDR's (complementary determining region) of their heavy or light chain variable regions. The divalent cation stabilizing formulations of the invention are particularly useful with such types of antibodies because isoaspartyl formation in a CDR region can affect the antibody binding activity and/or potency. Therapeutic polypeptides solubilized or included in a formulation of the invention exhibit stability for long periods of time, allowing administration of a safe and effective amounts of a therapeutic polypeptide such as an antibody or other polypeptide.

In a further specific embodiment, the formulation of the invention can include a therapeutic polypeptide, such as an antibody, at concentration ranging from about 1-150 mg/mL, a buffer such as 5 mM-50 mM sodium acetate at a pH above 4.0 and less than 6.0, about 1-3% glycerol or other excipient, about 0.004-0.1% polysorbate 80 or other surfactant, and about 10-150 mM $CaCl_2$ to improve stability of the therapeutic polypeptide by reducing isomerization. In other specific embodiments, a particularly useful buffer pH is lower than the pI of the therapeutic polypeptide to reduce or prevent polypeptide precipitation that can be caused by metal ions or salts when the buffer pH approaches the polypeptide pI value.

In further specific embodiments, divalent cations can be included in other polypeptide formulations that exhibit optimal stabilizing capacity of polypeptides. Such other formulations that can be used in conjunction with the divalent cations or the divalent cation-containing formulations of the invention include, for example, formulations containing acetate, glutamate, succinate or propionate buffer systems having pH values between about 4.0-7.5 or such buffer systems having a pH less than 6.0.

A biopharmaceutical refers to a macromolecule or biopolymer such as a polypeptide, nucleic acid, carbohydrate or lipid, or building block thereof, that is intended for use as a pharmaceutical. A biopharmaceutical formulation refers to a pharmaceutically acceptable medium that is compatible with a biopharmaceutical and is safe and non-toxic when administered to humans.

As used herein, the term "antibody" is intended to mean a polypeptide product of B cells within the immunoglobulin class of polypeptides which is composed of heavy and light chains and able to bind with a specific molecular target or antigen. The term "monoclonal antibody" refers to an antibody that is the product of a single cell clone or hybridoma. The term also is intended to refer to an antibody produced recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. As described further below, antibody and monoclonal antibody characteristics are well known in the art.

Monoclonal antibodies can be prepared using a wide variety of methods known in the art including the use of hybridoma, recombinant, phage display and combinatorial antibody library methodologies, or a combination thereof. For example, monoclonal antibodies can be produced using hybridoma techniques including those known in the art and taught, for example, in Harlow and Lane., *Antibodies: A Laboratory Manual*, Cold Spring Harbor Laboratory Press (1989); Hammerling, et al., in: *Monoclonal Antibodies and T-Cell Hybridomas* 563-681, Elsevier, N.Y. (1981); Harlow et al., *Using Antibodies: A Laboratory Manual*, Cold Spring Harbor Laboratory Press (1999), and *Antibody Engineering: A Practical Guide*, C. A. K. Borrebaeck, Ed., W.H. Freeman and Co., Publishers, New York, pp. 103-120 (1991). Examples of known methods for producing monoclonal antibodies by recombinant, phage display and combinatorial antibody library methods, including libraries derived from immunized and naive animals can be found described in *Antibody Engineering: A Practical Guide*, C. A. K. Borrebaeck, Ed., supra. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

As used herein, the term "functional fragment" when used in reference to an antibody is intended to mean a portion of an antibody which still retains some or all of its specific antigen binding activity. Such functional fragments can include, for example, antibody functional fragments such as Fd, Fv, Fab, F(ab'), F(ab)$_2$, F(ab')$_2$, single chain Fv (scFv), chimeric antibodies, diabodies, triabodies, tetrabodies and minibody. Other functional fragments can include, for example, heavy (H) or light (L) chain polypeptides, variable heavy ($V_H$) and variable light ($V_L$) chain region polypeptides, complementarity determining region (CDR) polypeptides, single domain antibodies, and polypeptides that contain at least a portion of an immunoglobulin that is sufficient to retain its specific binding activity. Such antibody binding fragments can be found described in, for example, Harlow and Lane, supra; *Molec. Biology and Biotechnology: A Comprehensive Desk Reference* (Myers, R. A. (ed.), New York: VCH Publisher, Inc.); Huston et al., *Cell Biophysics,* 22:189-224 (1993); Plückthun and Skerra, *Meth. Enzymol.,* 178:497-515 (1989) and in Day, E. D., *Advanced Immunochemistry*, Second Ed., Wiley-Liss, Inc., New York, N.Y. (1990).

With respect to antibodies and functional fragments thereof, various forms, alterations and modifications are well known in the art. The monoclonal antibodies of the invention can include any of such various monoclonal antibody forms, alterations and modifications. Examples of such various forms and terms as they are known in the art are set forth below.

A Fab fragment refers to a monovalent fragment consisting of the $V_L$, $V_H$, $C_L$ and $C_H1$ domains; a F(ab')$_2$ fragment is a bivalent fragment comprising two Fab fragments linked by a disulfide bridge at the hinge region; a Fd fragment consists of the $V_H$ and $C_H1$ domains; an Fv fragment consists of the $V_L$ and $V_H$ domains of a single arm of an antibody; and a dAb fragment (Ward et al., *Nature* 341:544-546, (1989)) consists of a $V_H$ domain.

An antibody can have one or more binding sites. If there is more than one binding site, the binding sites may be identical to one another or may be different. For example, a naturally occurring immunoglobulin has two identical binding sites, a single-chain antibody or Fab fragment has one binding site, while a "bispecific" or "bifunctional" antibody has two different binding sites.

A single-chain antibody (scFv) refers to an antibody in which a $V_L$ and a $V_H$ region are joined via a linker (e.g., a synthetic sequence of amino acid residues) to form a continuous polypeptide chain wherein the linker is long enough to allow the protein chain to fold back on itself and form a monovalent antigen binding site (see, e.g., Bird et al., *Science* 242:423-26 (1988) and Huston et al., *Proc. Natl. Acad. Sci. USA* 85:5879-83 (1988)). Diabodies refer to bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., *Proc. Natl. Acad. Sci. USA* 90:6444-48 (1993), and Poljak et al., *Structure* 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

A CDR refers to a region containing one of three hypervariable loops (H1, H2 or H3) within the non-framework region of the immunoglobulin (Ig or antibody) $V_H$ β-sheet framework, or a region containing one of three hypervariable loops (L1, L2 or L3) within the non-framework region of the antibody $V_L$ β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a loop varies in different antibodies, additional loop residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to either the Kabat (hypervariable) or Chothia (structural) designations, are set forth in the table below.

TABLE i. CDR Definitions

| | a. Kabat[1] | Chothia[2] | Loop Location |
|---|---|---|---|
| ii. $V_H$ CDR1 | 31-35 | 26-32 | linking B and C strands |
| iii. $V_H$ CDR2 | 50-65 | 53-55 | linking C' and C" strands |
| iv. $V_H$ CDR3 | 95-102 | 96-101 | linking F and G strands |
| v. $V_L$ CDR1 | 24-34 | 26-32 | linking B and C strands |
| vi. $V_L$ CDR2 | 50-56 | 50-52 | linking C' and C" strands |
| vii. $V_L$ CDR3 | 89-97 | 91-96 | linking F and G strands |

2. [1]Residue numbering follows the nomenclature of Kabat et al., supra
3. [2]Residue numbering follows the nomenclature of Chothia et al., supra A chimeric antibody refers to an antibody that contains one or more regions from one antibody and one or more regions from one or more other antibodies. In one specific example, one or more of the CDRs are derived from a non-human donor antibody having specific activity to EGFR and the variable region framework is derived from a human recipient antibody. In another specific example, all of the CDRs are derived from a non-human donor antibody having specific activity to EGFR and the variable region framework is derived from a human recipient antibody. In yet another specific example, the CDRs from more than one non-human EGFR-specific antibodies are mixed and matched in a chimeric antibody. For instance, a chimeric antibody can include a CDR1 from the light chain of a first non-human EGFR-specific antibody, a CDR2 and a CDR3 from the light chain of a second non-human EGFR-specific antibody and the CDRs from the heavy chain from a third EGFR-specific antibody. Further, the framework regions can be derived from one of the same or from one or more different human antibodies or from a humanized antibody. Chimeric antibodies can be produced where both the donor and recipient antibodies are human.

A humanized antibody or grafted antibody has a sequence that differs from a non-human species antibody sequence by one or more amino acid substitutions, deletions, and/or additions, such that the humanized antibody is less likely to induce an immune response, and/or induces a less severe immune response, as compared to the non-human species antibody, when it is administered to a human subject. In one specific example, certain amino acids in the framework and constant domains of the heavy and/or light chains of the non-human species antibody are changed to produce the humanized antibody. In another specific example, the constant domain(s) from a human antibody are fused to the variable domain(s) of a non-human species. Examples of how to make humanized antibodies may be found in U.S. Pat. Nos. 6,054,297, 5,886,152 and 5,877,293. Humanized antibodies also include antibodies produced using antibody resurfacing methods and the like.

A human antibody refers to antibodies that have one or more variable and constant regions derived from human immunoglobulin sequences. For example, a fully human antibody includes an antibody where all of the variable and constant domains are derived from human immunoglobulin sequences. Human antibodies can be prepared using a variety of methods known in the art. A specific example of a human antibody is panitumumab, which is the subject matter of the human anti-EGFR antibody described in U.S. Pat. No. 6,235,883. Panitumumab also is known in the art as Vectibix™ (Amgen, Thousand Oaks, Calif.) and is useful for treating pathological conditions such as metastatic colorectal cancer, for example.

One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to specifically bind to a particular antigen of interest.

A neutralizing antibody or an inhibitory antibody when used in reference to an formulated antibody of the invention refers to an antibody that inhibits the binding of receptor to ligand. In the specific example of an EGFR-specific monoclonal antibody, an inhibitory antibody refers to a monoclonal antibody that inhibits the binding of EGFR to EGF when an excess of the EGFR-specific antibody reduces the amount of EGF bound to EGFR. Binding inhibition can occur by at least 10%, particularly by at least about 20%. In various specific examples, the monoclonal antibody can reduce the amount of EGF bound to EGFR by, for example, at least 30%, 40%, 50%, 60%, 70%, 75%, 80%, 85%, 90%, 95%, 97%, 99%, and 99.9%. The binding reduction may be measured by any means known to one of ordinary skill in the art, for example, as measured in an in vitro competitive binding assay.

An "antagonistic" antibody refers to an antibody that inhibits an activity response of its antigen. In the specific example of an EGFR-specific monoclonal antibody, an antagonistic antibody refers to an antibody that inhibits the activity of EGFR when added to a cell, tissue or organism expressing EGFR. Diminution in activity can be by at least about 5%, particularly by at least about 10%, more particularly, by at least about 15% or more, compared to the level of EGFR activity in the presence of EGF alone. In various specific examples, the EGFR-specific monoclonal antibodies of the invention can inhibit the EGFR activity by at least about 20%, 30%, 40%, 50%, 60%, 70%, 80%, 90% or 100%.

An agonist antibody refers to an antibody that activates an activity response of its antigen. In the specific example of an EGFR-specific monoclonal antibody, an agonist antibody refers to an antibody that activates EGFR by at least about 5%, particularly by at least about 10%, more particularly, by at least about 15% when added to a cell, tissue or organism expressing EGFR, where "100% activation" is the level of activation achieved under physiological conditions by the same molar amount of EGF. In various specific examples, the KGFR-specific monoclonal antibodies of the invention can activate EGFR activity by at least about 20%, 30%, 40%, 50%, 60%, 70%, 80%, 90%, 100%, 125%, 150%, 175%, 200%, 250%, 300%, 350%, 400%, 450%, 500%, 750% or 1000%.

An epitope refers to a part of a molecule, for example, a portion of a polypeptide, that specifically binds to one or more antibodies within the antigen binding site of the antibody. Epitopic determinants can include continuous or non-continuous regions of the molecule that binds to an antibody. Epitopic determinants also can include chemically active surface groupings of molecules such as amino acids or sugar side chains and have specific three dimensional structural characteristics and/or specific charge characteristics.

As used herein, the term "specific" when used in reference to a monoclonal antibody binding activity is intended to mean that the referenced monoclonal antibody exhibits preferential binding for its antigen compared to other similar antigens. In the specific example of an EGFR-specific monoclonal antibody, specific binding activity is intended to mean that the referenced EGFR monoclonal antibody exhibits preferential binding for EGFR compared to other receptors related to epidermal growth factor. Preferential binding includes a monoclonal antibody of the invention exhibiting detectable binding to EGFR while exhibiting little or no detectable binding to another a related growth factor receptor.

As used herein, the term "epidermal growth factor receptor" or "EGFR" is intended to mean the art receptor that can be found expressed on the surface of epidermal cells and with binds to epidermal growth factor (EGF) and/or transforming growth factor alpha (TGFα). This receptor is well known in the art and can be found described in, for example, Yarden, Y., and Sliwkowski, M. X., *Nat Rev Mol Cell Biol.* 2, 127-37 (2001), and Mendelsohn, J. and Baselga, J., *J Clin Oncol* 21, 2787-99 (2003). EGFR also is the antigen for the panitumumab human antibody, which is the subject matter of U.S. Pat. No. 6,235,883.

As used herein, the term "divalent cation" is intended to mean a positively charged element, atom or molecule having a valence of plus 2. The term includes metal ions such as $Ca^{+2}$, $Zn^{+2}$, $Mn^{+2}$, $Mg^{+2}$, $Fe^{+2}$, $Co^{+2}$, $Ni^{+2}$ and/or $Cu^{+2}$. Divalent cations of the invention also include salt forms of the ions. Specific examples of divalent salt forms include $CaCl_2$, $ZnCl_2$, $MnSO_4$, $MnCl_2$ and $MgCl_2$ and other combinations of the above exemplary divalent cations in a salt form with, for example, chloride (Cl), sulfate ($SO_4$), acetate (Ac) and/or phosphate (P). Divalent cations and salt forms other than those exemplified above are well known in the art and included in the meaning of the term as it is used herein.

As used herein, the term "buffer" is intended to mean a substance that stabilizes the pH of a liquid, either its acidity or alkalinity. The term as it is used herein is intended to refer to a solution having a buffering substance, such as an acid, in equilibrium with its conjugate base. Exemplary buffers useful in a formulation of the invention include an acetic acid or acetate buffer, a glutamic acid or glutamate buffer, a succinic acid or succinate buffer, or a propionic acid or propionate buffer. These buffers, the terms are exemplified and used herein, refer to a buffer containing acetic acid, glutamic acid, succinic acid or propionic acid in equilibrium with its respective conjugate base. Each of these buffers can provide optimal buffer capacity in the region of their $pK_a$, where buffer capacity refers to a resistance to change in pH when perturbed with either acid or base added to the solution.

Acetic acid refers to an acid having the formula $CH_3COOH$, a melting point of 16.7° C. and a boiling point of 118.0° C. The $pK_a$ of acetic acid is 4.75. Glutamic acid refers to an acidic amino acid having the formula $C_5H_9NO_4$ and includes both L and D forms of the amino acid. The $pK_a$ the glutamic acid side chain is 4.07 whereas the $pK_a$ of succinic acid is 4.19 and 5.57 for its two carboxylic acid moieties. Succinic acid refers to a dicarboxylic acid having the formula $C_4H_6O_4$, a melting point of 185° C. and a boiling point of 235° C. Propionic acid refers to a liquid acid having the formula $CH_3CH_2COOH$, a melting point of 21° C. and a boiling point of 141° C. The acetic acid form of an acetic acid buffer of the invention can include, for example, acetic acid, acetate ion and/or acetate including acetic acid salt forms. Similarly, the glutamic acid form of a glutamic acid buffer of the invention can include, for example, glutamic acid, glutamate ion and/or glutamate including glutamic acid salt forms. The succinic acid form of a succinic acid buffer of the invention can include, for example, succinic acid, succinate ion and/or succinate including succinic acid salt forms. Further, the propionic acid form of a propionic acid buffer of the invention can include, for example, propionic acid, propionate ion having the formula $C_2H_5CO_2^-$ and/or propionate including propionic acid salt forms.

Exemplary salt forms of buffers that can be included in a buffer of the invention include, for example, sodium, potassium, calcium, organic amino or magnesium salt. Acetic acid, acetic acid buffers, glutamic acid, glutamic acid buffers, succinic acid, succinic acid buffers, propionic acid and propionic acid buffers are well known by those skilled in the art. The term "buffer" as it is used herein also is intended to include all buffers other than those exemplified above well known to those skilled in the art and applicable for use with biopharmaceuticals such as therapeutic polypeptides. Given the teachings and guidance provided herein, those skilled in the art will understand that buffers other than acetate, glutamate and/or succinate can be equally substituted in the formulations of the invention to maintain or enhance the stability of a therapeutic polypeptide.

As used herein, the term "excipient" is intended to mean a therapeutically inactive substance. Excipients can be included in a formulation for a wide variety of purposes including, for example, as a diluent, vehicle, buffer, stabilizer, tonicity agent, bulking agent, surfactant, cryoprotectant, lyoprotectant, anti-oxidant, metal ion source, chelating agent and/or preservative. Excipients include, for example, polyols such as sorbitol or mannitol; sugars such as sucrose, lactose or dextrose; polymers such as polyethylene glycol; salts such as NaCl, KCl or calcium phosphate, amino acids such as glycine, methionine or glutamic acid, surfactants, metal ions, buffer salts such as propionate, acetate or succinate, preservatives and polypeptides such as human serum albumin, as well as saline and water. Particularly useful excipients of the invention include sugars including sugar alcohols, reducing sugars, non-reducing sugars and sugar acids. Excipients are well known in the art and can be found described in, for example, Wang W., *Int. J. Pharm.* 185:129-88 (1999) and Wang W., *Int. J. Pharm.* 203:1-60 (2000).

Briefly, sugar alcohols, also known as a polyols, polyhydric alcohols, or polyalcohols, are hydrogenated forms of carbohydrate having a carbonyl group reduced to a primary or secondary hydroxyl group. Polyols can be used as stabilizing excipients and/or isotonicity agents in both liquid and lyophilized formulations. Polyols can protect polypeptides from both physical and chemical degradation pathways. Preferentially excluded co-solvents increase the effective surface tension of solvent at the protein interface whereby the most energetically favorable structural conformations are those with the smallest surface areas. Specific examples of sugar alcohols include sorbitol, glycerol, mannitol, xylitol, maltitol, lactitol, erythritol and threitol.

Reducing sugars include, for example, sugars with a ketone or aldehyde group and contain a reactive hemiacetal group, which allows the sugar to act as a reducing agent. Specific examples of reducing sugars include fructose, glucose, glyceraldehyde, lactose, arabinose, mannose, xylose, ribose, rhamnose, galactose and maltose.

Non-reducing sugars contain an anomeric carbon that is an acetal and is not substantially reactive with amino acids or polypeptides to initiate a Maillard reaction. Sugars that reduce Fehling's solution or Tollen's reagent also are known as reducing sugars. Specific examples of non-reducing sugars include sucrose, trehalose, sorbose, sucralose, melezitose and raffinose.

Sugar acids include, for example, saccharic acids, gluconate and other polyhydroxy sugars and salts thereof.

Buffer excipients maintain the pH of liquid formulations through product shelf-life and maintain the pH of lyophilized formulations during the lyophilization process and upon reconstitution, for example.

Tonicity agents and/or stabilizers included in liquid formulations can be used, for example, to provide isotonicity, hypotonicity or hypertonicity to a formulation such that it is suitable for administration. Such excipients also can be used, for example, to facilitate maintenance of a polypeptides' structure and/or to minimize electrostatic, solution protein-protein interactions. Specific examples of tonicity agents and/or stabilizers include polyols, salts and/or amino acids. Tonicity agents and/or stabilizers included in lyophilized formulations can be used, for example, as a cryoprotectant to guard polypeptides from freezing stresses or as a lyoprotectant to stabilize polypeptides in the freeze-dried state. Specific examples of such cryo- and lyoprotectants include polyols, sugars and polymers.

Bulking or caking agents are useful in lyophilized formulations to, for example, enhance product elegance and to prevent blowout. Bulking agents provide structural strength to the lyo cake and include, for example, mannitol and glycine.

Anti-oxidants are useful in liquid formulations to control protein oxidation and also can be used in lyophilized formulations to retard oxidation reactions.

Metal ions can be included in a liquid formulation, for example, as a co-factor and divalent cations such as calcium, zinc, manganese and magnesium can be utilized in suspension formulations as, for example, a stabilizer against isoaspartic acid formation as described herein. Chelating agents included in liquid formulations can be used, for example, to inhibit metal ion catalyzed reactions. With respect to lyophilized formulations, metal ions also can be included, for example, as a co-factor or as a stabilizer against isoaspartic acid formation as described herein. Although chelating agents are generally omitted from lyophilized formulations, they also can be included as desired to reduce catalytic reactions during the lyophilization process and upon reconstitution.

Preservatives included in liquid and/or lyophilized formulations can be used, for example, to protect against microbial growth and are particularly beneficial in multi-dose formulations. In lyophilized formulations, preservatives are generally included in the reconstitution diluent. Benzyl alcohol is a specific example of a preservative useful in a formulation of the invention.

As used herein, the term "surfactant" is intended to mean a substance that functions to reduce the surface tension of a liquid in which it is dissolved. Surfactants can be included in a formulation for a variety of purposes including, for example, to prevent or control aggregation, particle formation and/or surface adsorption in liquid formulations or to prevent or control these phenomena during the lyophilization and/or reconstitution process in lyophilized formulations. Surfactants include, for example, amphipathic organic compounds that exhibit partial solubility in both organic solvents and aqueous solutions. General characteristics of surfactants include their ability to reduce the surface tension of water, reduce the interfacial tension between oil and water and also form micelles. Surfactants of the invention include non-ionic and ionic surfactants. Surfactants are well known in the art and can be found described in, for example, Randolph T. W. and Jones L. S., Surfactant-protein interactions. *Pharm Biotechnol.* 13:159-75 (2002).

Briefly, non-ionic surfactants include, for example, alkyl poly(ethylene oxide), alkyl polyglucosides such as octyl glucoside and decyl maltoside, fatty alcohols such as cetyl alcohol and oleyl alcohol, cocamide MEA, cocamide DEA, and cocamide TEA. Specific examples of non-ionic surfactants include the polysorbates including, for example, polysorbate 20, polysorbate 28, polysorbate 40, polysorbate 60, polysorbate 65, polysorbate 80, polysorbate 81, polysorbate 85 and the like; the poloxamers including, for example, poloxamer 188, also known as poloxalkol or poly(ethylene oxide)-poly(propylene oxide), poloxamer 407 or polyethylene-polypropylene glycol and the like, and polyethylene glycol (PEG). Polysorbate 20 is synonymous with TWEEN 20, sorbitan monolaurate and polyoxyethylenesorbitan monolaurate.

Ionic surfactants include, for example, anionic, cationic and zwitterionic surfactants. Anionic surfactants include, for example, sulfonate-based or carboxylate-based surfactants such as soaps, fatty acid salts, sodium dodecyl sulfate (SDS), ammonium lauryl sulfate and other alkyl sulfate salts. Cationic surfactants include, for example, quaternary ammonium-based surfactants such as cetyl trimethylammonium bromide (CTAB), other alkyltrimethylammonium salts, cetyl pyridinium chloride, polyethoxylated tallow amine (POEA) and benzalkonium chloride. Zwitterionic or amphoteric surfactants include, for example, dodecyl betaine, dodecyl dimethylamine oxide, cocamidopropyl betaine and coco ampho glycinate.

As used herein, the term "therapeutic" when used in reference to a polypeptide of the invention, including an antibody of the invention, is intended to mean that the polypeptide is intended for use in the cure, mitigation, treatment or prevention of disease in a human or other animal. Accordingly, a therapeutic polypeptide is a specific type of pharmaceutical and can include a single polypeptide or two or more polypeptide subunits. A therapeutic polypeptide includes an antibody, a functional antibody fragment thereof, a peptibody or functional fragment thereof, growth factors, cytokines, cell signaling molecules and hormones. A wide variety of therapeutic polypeptides are well know in the art, all of which are included within the meaning of the term as it is used herein. Exemplary therapeutic polypeptides that can be used in a formulation of the invention include, for example, antibodies such as panitumumab (Vectibix™) and Epratuzumab® (Emab) as well as functional fragments to a wide variety of antigens, interleukins, G-CSF, GM-CSF, kinases, TNF and TNFR ligands, cyclins and erythropoietin.

As used herein, the term "effective amount" when used in reference to a therapeutic macromolecule such as a therapeutic polypeptide is intended to mean an amount of the therapeutic molecule sufficient to ameliorate at least one symptom associated with a targeted disease or physiological condition.

The invention provides a formulation including a buffer having a pH less than 6.0, a divalent cation between about 5-150 mM, an excipient comprising a sugar or polyol and an effective amount of a therapeutic polypeptide. The therapeutic polypeptide can be a therapeutic antibody, including an antibody having specific binding activity to human epidermal growth factor receptor (EGFR).

Figure 13:
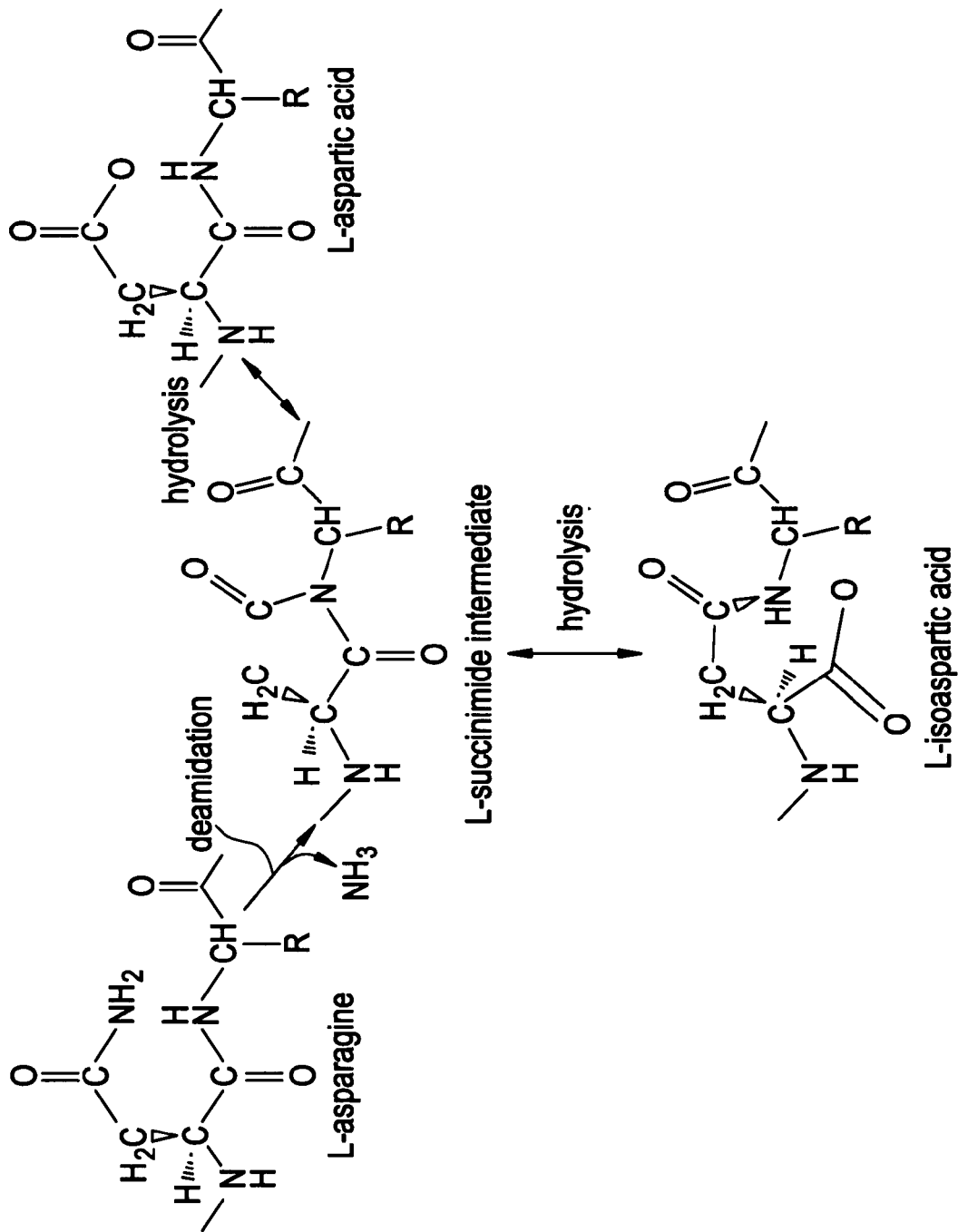
FIG. 13 is a schematic diagram showing the succinimide mediated degradation pathway of asparagine and aspartyl residues via isomerization into isoaspartic acid.

In one embodiment, a formulation of the invention is provided that inhibits or reduces the rate or extent of isoaspartic acid formation in polypeptides containing aspartic acid (Asp or D) and/or asparagine (Asn or N). FIG. 13 is a schematic diagram of the pathway of Asp or Asn isomerization to isoaspartic acid through an succinimide intermediate. Formation of isoaspartic acid can result in breakdown and instability of the polypeptide as well as reduction in biological activity.

Polypeptides containing Asp or Asn are further prone or susceptible to isomerization when, for example, the side chains of these amino acids are exposed to solvent. Other characteristics of polypeptides being susceptible to isomerization include, for example, Asp or Asn in close proximity to another charged or polar amino acid side chain such as glutamic acid (Glu or E), histidine (H is or H), lysine (Lys or K), serine (Ser or S) or theonine (Thr or T). Susceptibility to isomerization through a succinimide intermediate, for example, also can occur when neutral amino acid such as glycine (Gly or G) are in close proximity because of enhanced flexibility to the backbone and increased solvent exposure. Generally, the more solvent exposed or the closer in proximity an Asp residue is, for example, to solvent or another positively charged side chain, the more susceptible that residue is to isomerization. For example, Asp's or Asn's can be exposed to solvent in the CDRs of antibodies, in the β turns of immunoglobulin domain-containing polypeptides or in other regions having non-regular structure. A specific example of an antibody having an Asp residue in its CDR which isomerizes to isoaspartic acid is the antibody panitumumab. Further, for example, positively charged residues as close as 1, 2, 3 or 4 or more can facilitate isomerization and susceptibility of the polypeptide to isoaspartic acid formation. Similarly, residues such as those exemplified above in close proximity to an Asp, for example, or in close proximity within the three-dimensional structure of the polypeptide also can facilitate isoaspartic acid formation.

The inclusion of divalent cations in the formulations of the invention reduces the susceptibility of polypeptides containing one or more Asp or Asn residues to isomerization and isoaspartic acid formation. Similarly, the inclusion of divalent cations in the formulations of the invention reduces isoaspartic acid formation in polypeptides susceptible to isomerization. Inclusion of divalent cations is particularly useful in larger polypeptides having complex structures where, for example, one or more Asp or Asn residues can be susceptible to isomerization as described herein. Therefore, a divalent cation stabilizing formulation of the invention can be used with polypeptides ranging from 10 to hundreds or more amino acid residues. Accordingly, the divalent cation formulations of the invention can be used with polypeptides having, for example, 10, 20, 30, 40, 50, 60, 70, 80, 90, 100, 150, 200, 250, 300, 350, 400, 450, 500, 750 or 1000 or more amino acid residues. All sizes of polypeptides in between these exemplary numbers also are for use in the divalent cation-containing formulations of the invention.

A divalent cation formulation of the invention is useful for stabilizing and reducing isomerization of a polypeptide having 1, 2, 3, 4, 5, 6, 7, 8, 9 or 10 or more Asp and/or Asn residues. Similarly, a divalent cation formulation of the invention also is particularly useful for stabilizing and reducing isomerization of a polypeptide having an 1, 2, 3, 4, 5, 6, 7, 8, 9 or 10 or more Asp and/or Asn residues in close proximity to, for example, Glu, His, Lys, Ser, Thr, and/or Gly. Such residues can occur, for example, adjacent to each other such as in the exemplary motifs DD, DE, DH, DK, DS, DT or DG, (or ND, NN, NE, NH, NK and the like) or they can be, for example, 2, 3 or 4 or more residues apart as exemplified above. Similarly, multiple residues can occur adjacent or in close proximity such as in the motifs DDD, DDE, DED, DXD or DXE, where X represents any amino acid. Further, all combinations and permutations of the motifs exemplified above also can cause susceptibility to Asp or Asn isomerization. A specific example of a polypeptide having one of the motifs exemplified above is the antibody panitumumab, which contains a His adjacent to Asp 92 in CDR 3 which can isomerize to isoaspartic acid. The divalent cation formulations of the invention are useful for stabilizing polypeptides containing any of these motifs, combinations and/or permutations.

A formulation of the invention that inhibits or reduces the rate or extent of isoaspartic acid formation in polypeptides containing Asp or Asn includes an amount of a divalent cation sufficient to reduce isomerization and isoaspartic acid formation. Formulations of the invention containing an amount of divalent cation sufficient to reduce isomerization and isoaspartic acid formation are particularly useful with Asp or Asn containing polypeptides that are susceptible to isomerization such as those polypeptides having Asp or Asn containing motif exemplified above. Divalent cations can, for example, bind to amino acid residues where, for example, the polypeptide backbone carbonyls are not engaged in secondary structure formation and, thus, available to interact with divalent cations. Inclusion of divalent cations in a formulation of the invention also can, for example, stabilize polypeptide structure by reducing deamidation of Asn and/or hydrolysis of Asp. The side chains of, for example, aspartyl and glutamyl residues also can, for example, bind with divalent cations to prevent them from forming succinimide intermediates.

An amount of divalent cation, or salt form thereof, sufficient to inhibit or reduce susceptibility to isomerization and isoaspartic acid formation can include an amount between about 5-200 mM. In particular, retention in polypeptide stability and reduction in the rate or extent of Asp or Asn isomerization can be accomplished by including divalent cations at a concentration of between about 10-175 mM, 15-150 mM, 20-125 mM, 25-100 mM, 30-80 mM, 35-60 mM or 40-50 mM. Particularly useful divalent cation concentrations, or salt forms thereof, include, for example, 5, 10, 15, 20, 25, 30, 35, 40, 45, 50, 55, 60, 65, 70, 75, 80, 85, 90, 95, 100, 105, 110, 115, 120, 125, 130, 135, 140, 145 or 150 mM. All concentrations above, below and in between these exemplary divalent cation concentrations also can be employed in a formulation of the invention to inhibit or reduce the rate or extent of isomerization. Given the teachings and guidance provided herein, those skilled in the art will know how to select a particular divalent cation concentration, or salt form thereof, to inhibit or reduce polypeptide isomerization and, thus, increase the stability of the polypeptide in an aqueous or other liquid formulation.

Any of a variety of divalent cations, or salt forms thereof, can be used in a formulation of the invention. Exemplary divalent cations include, for example, those exemplified previously such as $Ca^{+2}$, $Zn^{+2}$, $Mn^{+2}$, $Mg^{+2}$, $Fe^{+2}$, $Co^{+2}$, $Ni^{+2}$ and/or $Cu^{+2}$. Other divalent cations include, for example, $Sc^{+2}$, $Ti^{+2}$, $V^{+2}$, $Cr^{+2}$, $Fe^{+2}$, $Co^{+2}$, $Ni^{+2}$, $Cu^{+2}$, $Ga^{+2}$, $Ge^{+2}$, and/or $Se^{+2}$ Salt forms of these exemplary divalent cations include, for example, $CaCl_2$, $ZnCl_2$, $MnSO_4$, $MnCl_2$ and $MgCl_2$ and other combinations of the above exemplary divalent cations in a salt form with, for example, chloride (Cl), sulfate ($SO_4$), acetate and/or phosphate. Given the teachings and guidance provided herein, those skilled in the art will know which divalent cations are useful for therapeutic formulations and which can be used for, for example, diagnostic or research applications. For example, divalent cations that can be less useful for therapeutic purposes can alternatively be used for stabilizing polypeptides in imaging procedures, other diagnostic procedures and/or for manipulation or storage of polypeptides used in preclinical research.

In a further embodiment, a formulation of the invention is buffered to have a pH that is less than the isoelectric point (pI) of the polypeptide or polypeptides included in the formulation. A formulation having a pH lower than the pI of included polypeptide is particularly useful to prevent or reduce polypeptide precipitation from the solution. Acidic pH's, including acidic pH's below the pI of an included polypeptide, also are particularly useful because lower pH buffers further promote stability of the polypeptide by preventing or reducing aggregation and other polypeptide degradation pathways as described further below. For example, and as described further below, in some embodiments of the invention, stable polypeptide formulations are used that have a pH less than 6.0 irrespective of the pI of the included polypeptide. In these specific embodiments, the pH can be between about 4.0-5.9. Particularly useful pH ranges include, for example, a pH less than 5.8 and a pH between about 4.8-5.2.

Formulations having a pH lower than the pI of the included polypeptide can range from about 4.0 to 8.0. As described further below, particularly useful pH ranges, including pH ranges below the pI of a polypeptide, include from about 4.0 to less than 6.0. In one exemplary embodiment, the polypeptide is panitumumab, which has calculated a pI of 6.63. In this specific embodiment, a buffer having a pH less than about 6.6 will be below panitumumab's pI and prevent or reduce precipitation of this polypeptide in a divalent cation-containing formulation of the invention. In a further embodiment, the pI of the formulated polypeptide can be, for example, 6.0, 6.5, 7.0 or greater and the pH of the final formulation can be, for example, less than 6.0, 6.5 or 7.0. In other embodiments, the pI of polypeptides in a formulation of the invention can be, for example, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4 or 8.5 and the pH of a formulation of the invention can be used that is less than any of these exemplary pI values. Given the teachings and guidance provided herein, those skilled in the art will know how to select a pH value less than the pI of a polypeptide included in a divalent cation-containing formulation of the invention in order to facilitate prevention or reduction in polypeptide precipitation. Those skilled in the art also will understand that such embodiments having pH values lower than the pI of the polypeptide may or may not be needed in order to reduce precipitation and that it is well with the skill of one in the art to formulate a polypeptide at different pH values to determine whether such lower pH formulations are desired.

Divalent cations, or salt forms thereof, can be included in any desirable solution, buffer or formulation suitable for a therapeutic polypeptide and appropriate for storage, manipulation or administration to an individual as a pharmaceutical. Given the teachings and guidance provided herein, those skilled in the art will understand that inclusion of divalent cations in a polypeptide solution will prevent or reduce the rate or extent of Asp or Asn isomerization, succinimide intermediate and/or isoaspartic acid formation. A variety of polypeptide formulations conferring polypeptide stability are exemplified below that are useful for storage, manipulation or administration of therapeutic polypeptides. Inclusion of divalent cations is these exemplary formulations in a concentration between about 5-200 mM can further enhance stability of the polypeptide by preventing or reducing the rate or extent of isomerization. Those skilled in the art will understand that various formulations other than those exemplified below also can be used together with the divalent cations, or salt forms thereof, to further augment polypeptide stability by preventing or reducing the rate or extent of Asp or Asn isomerization.

For example, one exemplary formulation of the invention exhibits optimal properties for administration, storage and manipulation of polypeptides, including antibodies. A particularly useful polypeptide for use in a formulation of the invention is panitumumab. Manipulation includes, for example, lyophilization, reconstitution, dilution, titration and the like. The buffering component of a formulation of the invention is efficient to prepare using methods well known in the art and can easily be combined with a desired polypeptide using any of a variety of methods well know in the art, avoiding cumbersome and, sometimes lengthy, preparatory and/or intermediate steps. Additionally, the aqueous buffer component is selected to be compatible with a wide variety of excipients and surfactants that facilitate stability of a polypeptide. These and other attributes of a formulation of the invention described herein allow stable formulations of bioactive molecules to be prepared and maintained over periods exceeding 12-18 months or more.

Stability of a formulation of the invention, including a liquid formulation of the invention, refers to the retention of structure and/or function of a polypeptide within a formulation. A polypeptide in a formulation of the invention will exhibit attributes such as resistance to change or deterioration that affect stability or function and therefore maintain consistent functional characteristics over time. A polypeptide in a divalent cation, or salt form thereof, of the invention also will exhibit inhibition or reduction in the isomerization of Asp and/or Asn to isoaspartic acid. Accordingly, formulations of the invention will exhibit, for example, reliability and safety with respect to activity per volume or activity units.

In one embodiment, the stability of a polypeptide within a divalent cation-containing formulation of the invention will exhibit the prevention or reduction of Asp or Asn isomerization to isoaspartic acid, thus, reducing the rate or extent of subsequent degradation. Reduction in the rate or extent of isomerization includes, for example, inhibition of between about 20-100%, 40-95%, 50-90%, 60-85% or 70-80% of isoaspartic acid formation in the presence of a divalent cation compared to the absence of a divalent cation. Accordingly, stability of a polypeptide within a divalent cation-containing formulation of the invention includes inhibition of isoaspartic acid formation in the presence of divalent cation greater than 99.5%, at least about 99%, 98%, 97%, 96%, 95%, 94%, 93%, 92%, 91%, 90%, 89%, 88%, 87%, 86%, 85%, 84%, 83%, 82%, 81% or 80% compared to in the absence of divalent cation. The extent of inhibition can be determined by a variety of methods well known in the art and described further below. Specific examples of such measurements are exemplified in Example II.

In another embodiment, the stability of a polypeptide within a formulation of the invention includes, for example, the retention of physical and/or chemical stability. Polypeptide stability can be assessed by, for example, determining whether the polypeptide has been subjected to a physical degradation and/or chemical degradation pathway such as those described previously, including chemical modification of its structure. Retention in stability of a polypeptide in a formulation of the invention includes, for example, retention of physical or chemical stability between about 80-100%, 85-99%, 90-98%, 92-96% or 94-95% compared to the stability of the polypeptide at an initial time point. Accordingly, stability of a polypeptide within a formulation of the invention includes retention of stability greater than 99.5%, at least about 99%, 98%, 97%, 96%, 95%, 94%, 93%, 92%, 91%, 90%, 89%, 88%, 87%, 86%, 85%, 84%, 83%, 82%, 81% or 80% compared to the stability of the polypeptide at an initial time point.

In a further embodiment, stability of a polypeptide within a formulation of the invention includes, for example, retention of activity. Polypeptide activity can be assessed using, for example, an in vitro, in vivo and/or in situ assay indicative of the polypeptide's function. Retention of stability of a polypeptide in a formulation of the invention includes, for example, retention of activity between about 50-100% or more, depending on the variability of the assay. For example, retention in stability can include retention of activity between about 60-90% or 70-80% compared to the activity of the polypeptide at an initial time point. Accordingly, stability of a polypeptide within a formulation of the invention includes retention of activity of at least about 50%, 55%, 60%, 65%, 70%, 75%, 80%, 85%, 90%, 95% or 100% and can include activity measurements greater than 100% such as 105%, 110%, 115%, 120%, 125% or 150% or more compared to the activity of the polypeptide at an initial time point. Generally, an initial time point is selected to be the time that a polypeptide is first prepared in a formulation of the invention or first examined for quality (i.e., meets release specifications). An initial time point also can include the time at which a polypeptide is reformulated in a formulation of the invention. The reformulation can be, for example, at a higher concentration, lower concentration or at the same concentration of an initial preparation.

A formulation of the invention can be prepared to be isotonic with a reference solution or fluid (i.e., blood serum). An isotonic solution has a substantially similar amount of dissolved solute in it compared to the things around it so that it is osmotically stable. Unless expressly compared to a specific solution or fluid, isotonic or isotonicity is exemplary used herein by reference to human blood serum (e.g., 300 mOsmol/kg). Therefore, an isotonic formulation of the invention will contain a substantially similar concentration of solutes or exhibit substantially similar osmotic pressure as human blood. In general, an isotonic solution contains about the same concentration of solutes as normal saline for humans and many other mammals, which is about 0.9 weight percent (0.009 g/ml) salt in aqueous solution (e.g., 0.009 g/ml NaCl). Formulations of the invention also can include hypotonic or hypertonic solution preparations.

A formulation of the invention can be prepared in any of a variety of ways well known in the art. A formulation of the invention will contain one or more divalent cations, or salt form thereof, in a concentration ranging from about 5-200 mM, a buffer component having a desired pH, at least one excipient and an effective amount of a polypeptide. Buffering capacity of a formulation of the invention is supplied by a weak acid or base in equilibrium with its conjugate base or acid, respectively. Buffer components exhibit strong buffering capacity at a pH range that is within about 1 pH unit of their respective $pK_a$s. In specific embodiments of the invention where an acidic pH is desired, acetic acid, glutamic acid, succinic acid or propionic acid have $pK_a$s which are optimal for many biological molecules including, for example, antibodies such as panitumumab. These exemplary buffers exhibit strong buffering capacity at pH ranges between, for example, 4.0-6.0, and are particularly useful for formulations having a pH below 6.0.

Any of a wide variety of buffer components well known in the art can be used in a formulation of the invention. Such buffer components include, for example, acetic acid, glutamic acid, succinic acid, propionic acid, maleic acid, gluconate, histidine or other amino acids, citrate, phosphate, or salt forms thereof. A wide variety of other buffers including, for example, other organic acids, are well known in the art and can similarly be used as a buffer component in a formulation of the invention. Given the teachings and guidance provided herein, those skilled in the art will known that any of the above buffer components or others well known in the art can be selected and used in a formulation of the invention given the desired pH of the formulation and excipients, if any, included in the formulation.

The buffer component can be supplied to the buffering system in a variety of different forms. Such buffers and forms thereof are exemplified herein for the purpose of illustration with reference to acetic acid, glutamic acid or succinic acid-containing buffers. Acetic acid, glutamic acid and succinic acid buffers are well known in by those skilled in the art. As described previously, those skilled in the art will understand that any of a variety of other buffers well known in the art can be equally substituted for the exemplified acetic acid, glutamic acid and/or succinic acid buffers exemplified below. In certain specific embodiments, buffers employing histidine, citric acid and/or phosphate, or a salt thereof, will be not be selected in lieu of a buffer having more useful buffering characteristics at a desired pH.

For example, the acetic acid, glutamic acid or succinic acid component can be supplied as their acid, acid salt or any other form that is available or that can be produced using chemical synthesis. The acid salt forms of these acids—acetate, glutamate or succinate—are particularly useful for producing a buffering system of a formulation because they are commercially available in highly purified form. Acetate, glutamate and succinate salts include, for example, those described previously as well as others known in the art. A highly purified form of a formulation component refers to pharmaceutical grade purity level, which is sufficiently pure to administer to a human such that it is devoid of contaminants so as to be safe and non-toxic.

A formulation of the invention will contain a concentration of, for example, an acid or acid salt of the invention having sufficient buffering capacity to maintain a selected pH of a formulation at a selected temperature. Useful concentrations of acid or salt (e.g., acetic acid or acetate, glutamic acid or glutamate or succinic acid or succinate) include, for example, between about 1-150 mM and as high as 200 mM or more. For example, in some instances, it can be desirable to include up to 1 M acid or acid salt to produce a hypertonic formulation of the invention. Such hypertonic solutions can be diluted to produce an isotonic formulation prior to use if desired. By way of exemplification, useful concentrations of acid or acid salt buffer of the invention include, for example, between about 1-200 mM, 5-175 mM, 10-150 mM, 15-125 mM, 20-100 mM, 25-80 mM, 30-75 mM, 35-70 mM, 40-65 mM and 45-60 mM. Other useful concentrations of acid or acid salt include, for example, between about 1-50 mM, 2-30 mM, 3-20 mM, 4-10 mM and 5-8 mM. Accordingly, an acid or acid salt concentration of about 1, 2, 3, 4, 5, 6, 7, 8, 9, 10, 11, 12, 13, 14, 15, 16, 17, 18, 19 or 20 mM or more also are useful. All values above and below these exemplary concentrations also can be used in a formulation. Therefore, a formulation of the invention can have a acid or acid salt less than 1 mM or greater than 20 mM including, for example, 21, 22, 23, 24, 25, 30, 35, 40, 45 or 50 mM or more acid or acid salt. Various formulation are exemplified in the Example below and shown in FIGS. 1-13.

As described previously, the $pK_a$ of an acetic acid, glutamic acid, succinate acid or propionic acid buffer in a formulation of the invention is particularly suitable for use with polypeptides because they have strong buffering capacity between about pH 4.0-7.0, and particularly between about 4.0-6.0, which can be optimal for maintenance of polypeptide stability. A buffer component of a formulation of the invention can be prepared to exhibit any effective buffering capacity within a pH range of between about 4.0 to 7.0. Exemplary pH ranges of a buffer and/or the final formulation including, for example, an acetic acid, glutamic acid, succinic acid or propionic acid buffer can include pH ranges between about 3.5-6.5, between about 4.0-6.0, between about 4.5-5.5, between about 4.8-5.2 or about 5.0. Accordingly, a buffer and/or the final formulation can be prepared to have a pH of about 3.0 or less, about 3.5, 4.0, 4.5, 4.8, 5.0, 5.2, 5.5, 6.0, 6.5 or about 7.0 or more. All pH values above, below and in between these exemplary values also can be used in an acetic acid, glutamic acid or succinic acid buffer and/or the final formulation. Therefore, for example, a buffer component and/or the final formulation of the invention can be prepared to have a pH less than 3.5, greater than 6.5 and all values within these ranges. Those skilled in the art will understand that much of the strength of the buffering capacity of a buffer will decrease outside of about 1 pH unit of its $pK_a$ and, given the teachings and guidance provided herein, can determine whether inclusion of an acetic acid, glutamic acid or succinic acid buffer below a pH of about 3.5 or above a pH of about 6.5 is useful in a formulation of the invention.

In other embodiments, useful pH ranges of a formulation of the invention include acidic pH values. Formulations having acidic pH values confer useful characteristics onto the formulation such as increased stability of the included polypeptide and reduction in polypeptide precipitation in the presence of divalent cations as described and exemplified above and below. Exemplary acidic pH values include those described above and previously as well as formulations having a pH less than 6.0. Such formulations having acid pH's also include, for example, a pH of 5.9 or less, 5.8 or less, 5.7 or less, 5.5 or less, 5.4 or less, 5.3 or less, 5.2 or less, 5.1 or less, 5.0 or less, 4.9 or less, 4.8 or less, 4.7 or less, 4.6 or less, 4.5 or less, 4.4 or less, 4.3 or less, 4.2 or less, 4.1 or less or 4.0. Given the teachings and guidance provided herein, those skilled in the art will understand that an appropriate buffer component can be selected based on, for example, its $pK_a$ to maintain a formulation of the invention at any of the pH values exemplified above or other pH desired for the formulation.

A buffer component of a formulation of the invention can include one or more excipients. As described previously, one role of an included excipient is to provide stabilization of the polypeptide against stresses that can occur during manufacturing, shipping and storage. To accomplish this role, at least one excipient can function as a buffer, stabilizer, tonicity agent, bulking agent, surfactant, cryoprotectant, lyoprotectant, anti-oxidant, metal ion source, chelating agent and/or preservative. In addition, at least one excipient also can function as a diluent and/or vehicle or be employed to reduce viscosity in high concentration formulations in order to enable their delivery and/or enhance patient convenience.

Similarly, at least one excipient additionally can confer more than one of the above functions onto a formulation of the invention. Alternatively, two or more excipients can be included in a formulation of the invention to perform more than one of the above or other functions. For example, an excipient can be included as a component in a formulation of the invention to change, adjust or optimize the osmolality of the formulation, thereby acting as a tonicifier. Similarly, a tonicity agent and a surfactant can both be included in a formulation of the invention to both adjust the osmolality and control aggregation. Excipients, their use, formulation and characteristics are well known in the art and can be found described in, for example, Wang W., *Int. J. Pharm.* 185:129-88 (1999) and Wang W., *Int. J. Pharm.* 203:1-60 (2000).

In general, excipients can be chosen on the basis of the mechanisms by which they stabilize proteins against various chemical and physical stresses. As described herein, certain excipients are beneficial to include so as to alleviate the effects of a specific stress or to regulate a particular susceptibility of a specific polypeptide. Other excipients are beneficial to include because they have more general effects on the physical and covalent stabilities of proteins. Particularly useful excipients include those chemically and functionally innocuous or compatible with aqueous buffer solutions and polypeptides so as to optimize the stability properties of a formulation. Various such excipients are described herein as exemplary excipients exhibiting chemical compatibility with the aqueous formulations of the invention and functional compatibility with the polypeptide included in such formulations. Those skilled in the art will understand that the teachings and guidance provided herein with respect to the exemplified excipients are equally applicable to the use of a wide range of other excipients well known in the art.

For example, optimal excipients chosen to enhance or confer stability of a polypeptide within a formulation include those that are substantially free from reacting with functional groups on the polypeptide. In this regard, both reducing and non-reducing sugars can be used as an excipient in a formulation of the invention. However, because reducing sugars contain a hemiacetal group they can react and form adducts or other modifications with amino groups on amino acid side chains of polypeptides (i.e., glycosylation). Similarly, excipients such as citrate, succinate or histidine also can form adducts with amino acid side chains. Given the teachings and guidance provided herein, those skilled in the art will known that greater retention of stability for a given polypeptide can be achieved by choosing a non-reducing sugar over a reducing sugar or over other amino acid-reactive excipients such as those exemplified above.

Optimal excipients also are chosen to enhance or provide stabilization with reference to the mode of administration for an aqueous formulation of the invention. For example, parenteral routes of intravenous (IV), subcutaneous (SC) or intramuscular (IM) administration can be more safe and efficacious when all components of the formulation maintain physical and chemical stability during manufacture, storage and administration. Those skilled in the art will know to employ one or more excipients that maintain maximal stability of the active form of a polypeptide given, for example, a particular manufacturing or storage condition or a particular mode of administration. The excipients exemplified herein for use in a formulation exhibit these and other characteristics.

The amount or concentration of excipient to use in a formulation of the invention will vary depending on, for example, the amount of polypeptide included in the formulation, the amount of other excipients included in the desired formulation, whether a diluent is desired or needed, the amount or volume of other components of the formulation, the total amount of components within a formulation, the specific activity of the polypeptide and the desired tonicity or osmolality to be achieved. Specific examples for excipient concentrations are exemplified further below. Further, different types of excipients can be combined into a single formulation. Accordingly, a formulation of the invention can contain a single excipient, two, three or four or more different types of excipients. Combinations of excipients can be particularly useful in conjunction with a formulation that contains two or more different polypeptides. The excipients can exhibit similar or different chemical properties.

Given the teachings and guidance provided herein, those skilled in the art will know what amount or range of excipient can be included in any particular formulation to achieve a formulation of the invention that promotes retention in stability of the polypeptide. For example, the amount and type of a salt to be included in a formulation of the invention can be selected based on to the desired osmolality (i.e., isotonic, hypotonic or hypertonic) of the final solution as well as the amounts and osmolality of other components to be included in the formulation. Similarly, by exemplification with reference to the type of polyol or sugar included in a formulation, the amount of such an excipient will depend on its osmolality. Inclusion of about 5% sorbitol can achieve isotonicity while about 9% of a sucrose excipient is needed to achieve isotonicity. Selection of the amount or range of concentrations of one or more excipients that can be included within a formulation of the invention has been exemplified above by reference to salts, polyols and sugars. However, those skilled in the art will understand that the considerations described herein and further exemplified by reference to specific excipients are equally applicable to all types and combinations of excipients including, for example, salts, amino acids, other tonicity agents, surfactants, stabilizers, bulking agents, cryoprotectants, lyoprotectants, anti-oxidants, metal ions, chelating agents and/or preservatives.

Excipients can be included in a formulation of the invention at concentration ranges generally between about 1-40% (w/v), between about 5-35% (w/v), between about 10-30% (w/v), between about 15-25% (w/v) or about 20% (w/v). Concentrations as high as about 45% (w/v), 50% (w/v) or more than 50% (w/v) in certain instances also can be employed in the formulations of the invention. For example, in some instances, it can be desirable to include concentrations up to 60% (w/v) or 75% (w/v) to produce a hypertonic formulation of the invention. Such hypertonic solutions can be diluted to produce an isotonic formulation prior to use if desired. Other useful concentration ranges include between about 1-20%, particularly between about 2-18% (w/v), more particularly between about 4-16% (w/v), even more particularly between about 6-14% (w/v) or between about 8-12% (w/v) or about 10% (w/v). Excipient concentrations and/or amounts less than, greater than or in between these ranges also can be used in a formulation of the invention. For example, one or more excipients can be included in a formulation which constitute less than about 1% (w/v). Similarly, a formulation can contain a concentration of one or more excipients greater than about 40% (w/v). Accordingly, a formulation of the invention can be produced that contains essentially any desired concentration or amount of one or more excipients including, for example, 1, 2, 3, 4, 5, 6, 7, 8, 9, 10, 11, 12, 13, 14, 15, 16, 17, 18, 19 or 20% (w/v) or more. An example is provided below for a formulation of a polypeptide having about 10.0% excipient.

Various excipients useful in a formulation of the invention have been described previously. In the specific formulations described in the Example, exemplified excipients include glycerol, sucrose, trehalose and/or sorbitol, which is employed as a stabilizer. Another excipient exemplified in the formulations described in the Example is polysorbate 80, which is employed in liquid formulations compared to bulk formulations for storage. Other excipients useful in either a liquid or lyophilized formulation of the invention include, for example, fucose, cellobiose, maltotriose, melibiose, octulose, ribose, xylitol, arginine, histidine, glycine, alanine, methionine, glutamic acid, lysine, imidazole, glycylglycine, mannosylglycerate, Triton X-100, Pluoronic F-127, cellulose, cyclodextrin, dextran (10, 40 and/or 70 kD), polydextrose, maltodextrin, ficoll, gelatin, hydroxypropylmeth, sodium phosphate, potassium phosphate, $ZnCl_2$, zinc, zinc oxide, sodium citrate, trisodium citrate, tromethamine, copper, fibronectin, heparin, human serum albumin, protamine, glycerin, glycerol, EDTA, metacresol, benzyl alcohol and phenol. Excipients such as these as well as others known in the art can be found described in, for example, Wang W., supra, (1999) and Wang W., supra, (2000).

A buffer component of a formulation of the invention also can include one or more surfactants as an excipient. As described previously, one role of surfactants in a formulation of the invention is to prevent or minimize aggregation and/or adsorption such as surface-induced degradation. At sufficient concentrations, generally about the surfactant's critical micellar concentration, a surface layer of surfactant molecules serve to prevent protein molecules from adsorbing at the interface. Thereby, surface-induced degradation is minimized. Surfactant, their use, formulation and characteristics for formulations are well known in the art and can be found described in, for example, Randolph and Jones, supra, (2002).

Optimal surfactants to include in a formulation of the invention can be chosen, for example, to enhance or promote retention in stability of the polypeptide by preventing or reducing aggregation and/or adsorption. For example, sorbitan fatty acid esters such as the polysorbates are surfactants exhibiting with a wide range of hydrophilic and emulsifying characteristics. They can be used individually or in combination with other surfactants to cover a wide range of stabilization needs. Such characteristics are particularly suitable for use with polypeptides because they can be tailored to cover the wide range of hydrophobic and hydrophilic characteristics of polypeptides. Considerations for selecting a surfactant include those described previously with reference to excipients in general as well as the hydrophobic character and critical micellar concentration of the surfactant. The surfactants exemplified herein, as well as many others well known in the art can be used in a formulation of the invention.

Surfactant concentration ranges for a formulation of the invention include those described previously with reference to excipients in general with particularly useful concentrations being less than about 1% (w/v). In this regard, surfactant concentrations generally can be used at ranges between about 0.001-0.10% (w/v), particularly between about 0.002-0.05% (w/v), more particularly between about 0.003-0.01% (w/v), even more particularly between about 0.004-0.008% (w/v) or between about 0.005-0.006% (w/v). Surfactant concentrations and/or amounts less than, greater than or in between these ranges also can be used in a formulation of the invention. For example, one or more surfactants can be included in a formulation which constitute less than about 0.001% (w/v). Similarly, a formulation can contain a concentration of one or more surfactants greater than about 0.10% (w/v). Accordingly, a formulation of the invention can be produced that contains essentially any desired concentration or amount of one or more surfactants including, for example, 0.001, 0.002, 0.003, 0.004, 0.005, 0.006, 0.007, 0.008, 0.009, 0.010, 0.02, 0.03, 0.04, 0.05, 0.06, 0.07, 0.08, 0.09 or 0.10% (w/v) or more.

Various surfactants useful as an excipient in a formulation of the invention have been described previously. Other surfactants useful in either a liquid or lyophilized formulation of the invention include, for example, sugar esters such as esters lauric acid (C12), palmitic acid (C16), stearic acid (C18), macrogol cetostearyl ethers, macrogol lauryl ethers, macrogol oleyl ether, macrogol oleate, macrogol stearate, macrogol glycerol ricinoleate, macrogol glycerol hydroxystearate; alkyl polyglucosides such as octyl glucoside and decyl maltoside; fatty alcohols such as cetyl alcohol and oleyl alcohol, and cocamides such as cocamide MEA, DEA, TEA, other non-ionic surfactants and other ionic surfactants.

Therefore, the invention provides a formulation that includes an aqueous solution having between about 1-100 mM acetic acid, glutamic acid or succinic acid with a pH from about 4.5 to about 7.0, a polyol or sugar between about 1-20%, polysorbate 80 between about 0.001-0.010% and an effective amount of a therapeutic antibody. The formulation also can include one or more divalent cations at a concentration between 5-200 mM and/or a pH less than 6.0. The formulation of the invention also can include about 10 mM of acetic acid, glutamic acid or succinic acid having a pH of about 5.0, about 2.6% glycerol and about 0.004% polysorbate 80. Various other formulation components, combinations of components and concentrations thereof also can be included in a formulation of the invention.

Further provided is a formulation having a therapeutic polypeptide as the polypeptide component of the formulation. The formulation can include one or more divalent cations at a concentration between 5-200 mM and/or a pH less than 6.0. The therapeutic polypeptide includes an antibody, a functional fragment of an antibody, a peptibody, a hormone, a growth factor or a cell signaling molecule. In a specific embodiment, the antibody is a human antibody. In another specific embodiment, the antibody is specific for EGFR. In yet another specific embodiment, the antibody is panitumumab.

Also included within a formulation of the invention is a wide variety of therapeutic molecules. A therapeutic molecule of the invention includes, for example, a macromolecule or biopolymer such as a polypeptide, nucleic acid, lipid, carbohydrate employed as an active pharmaceutical ingredient or building block thereof, that can be used in the diagnosis, treatment or prevention of a pathological condition or as a component of a medication. For example, the formulations of the invention are applicable to, and facilitate retention in stability for, polypeptides, glycopolypeptides, peptidoglycans, DNA such as genomic DNA, cDNA and the like, RNA such as mRNA, RNAi, SNRPS, and the like, carbohydrates contemplated as an active pharmaceutical ingredient which can include monosaccharides, polysaccharides, N-linked sugars, O-linked sugars, leptins and the like, lipids such as phospholipids, glycolipids, fatty acids, polyamines, isoprenoids, amino acids, nucleotides, neurotransmitters and cofactors, as well as many other macromolecules, biopolymers and building blocks thereof, endogenous to mammalian physiological systems, including human. These and other biopharmaceuticals are well known to those skilled in the art and can be included in a formulation of the invention for use in the diagnosis, treatment or prevention of a pathological condition or as a component of a medication.

Given the teachings and guidance provided herein, those skilled in the art will understand that a formulation of the invention is equally applicable to all types of therapeutic molecules, including those exemplified above as well as others well known in the art. Given the teachings and guidance provided herein, those skilled in the art also will understand that the selection of, for example, type(s) or and/or amount(s) of one or more excipients, surfactants and/or optional components can be made based on the chemical and functional compatibility with the therapeutic molecule to be formulated and/or the mode of administration as well as other chemical, functional, physiological and/or medical factors well known in the art. For example, as described previously, non-reducing sugars exhibit favorable excipient properties when used with polypeptide therapeutics compared to reducing sugars. Accordingly, the formulations of the invention are exemplified further below with reference to polypeptide therapeutics. However, the range of applicability, chemical and physical properties, considerations and methodology applied to polypeptide therapeutics are similarly applicable to therapeutic molecules other than polypeptide therapeutics.

Exemplary types of polypeptides applicable for use in a formulation of the invention include all types of therapeutic polypeptides including, for example, the immunoglobulin superfamily of polypeptides, growth factors, cytokines, cell signaling molecules and hormones. Exemplary polypeptides applicable for use in a formulation of the invention include all therapeutic polypeptides including, for example, antibodies and functional fragments thereof, interleukins, G-CSF, GM-CSF, kinases, TNF and TNFR ligands including Fhm, cyclins, erythropoietin, nerve growth factors (NGF), developmentally regulated nerve growth factor VGF, neurotrophic factors, neurotrophic factor NNT-1, Eph receptor, Eph receptor ligands; Eph-like receptor, Eph-like receptor ligands, inhibitors of apoptosis proteins (IAP), Thy-1 specific protein, Hek ligand (hek-L), Elk receptor and Elk receptor ligands, STATs, collagenase inhibitor, osteoprotegerin (OPG), APRIL/G70, AGP-3/BLYS, BCMA, TACI, Her-2/neu, Apolipoprotein polyeptides, integrins, tissue inhibitor of metalloproteinases, C3b/C4b complement receptor, SHC binding protein, DKR polypeptides, extracellular matrix polypeptides, antibodies to the above therapeutic polypeptides and antibody functional fragments thereof, antibodies to receptors for the above therapeutic polypeptides and antibody functional fragments thereof, functional polypeptide fragments thereof, fusion polypeptides, chimeric polypeptides and the like.

Specific examples of commercially available pharmaceuticals applicable for use in a formulation of the invention include, for example, ENBREL (Etanercept; a CHO expressed dimeric fusion protein ((Amgen, Inc.)); EPOGEN (Epoetin alfa; a mammalian cell expressed glycoprotein (Amgen, Inc.)); INFERGEN® (Interferon alfacon-1; an *E. Coli* expressed recombinant protein (Amgen, Inc.)); KINERET® (anakinra; an *E. coli* expressed recombinant, nonglycosylated form of the human interleukin-1 receptor antagonist (IL-1Ra) (Amgen, Inc.)); ARANESP (darbepoetin alfa; a CHO expressed recombinant human erythropoiesis stimulating protein (Amgen, Inc.)); NEULASTA (peg-filgrastim; covalent conjugate of recombinant methionyl human G-CSF and 20 kD PEG (Amgen, Inc.)); NEUPOGEN (Filgrastim; an *E. coli* expressed human granulocyte colony-stimulating factor (G-CSF) (Amgen, Inc.)), and STEMGEN (Ancestim, stem cell factor; an *E. Coli* expressed recombinant human protein (Amgen, Inc.)). These and all other commercially available pharmaceuticals can be, for example, reformulated in a formulation of the invention at the time of production, prior to use and/or prior to short or long term storage.

1. Specific examples of antibodies, in particular antibodies specific to EGFR applicable, for use as a therapeutic antibody in a formulation of the invention include, for example, panitumumab (Amgen, Inc.); cetuximab (Erbitux®; Imclone Systems, New York City); IMC-11F8 (Imclone Systems); Humax-EGFR (Genmab, Copenhagen, Denmark); matuzumab (EMD-7200; Merck KGaA, Darmstadt, Germany), and nimotuzumab (TheraCIM hR3; YM Biosciences, Mississauga, Ontario, Canada). All of the above antibodies are well known in the art. For example, panitumumab is commercially available from Amgen and is the subject matter of the human anti-EGFR antibody described in U.S. Pat. No. 6,235,883. IMC-11F8 is the subject matter of U.S. Pat. No. 7,060,808 and Humax-EGFR is the subject matter of U.S. Patent Publications 20030091561 and 20030194403.

By further illustration of the range of therapeutic molecule applicability of a formulation of the invention, described further below are exemplary types of antibodies and functional fragments thereof, that can be employed as a therapeutic polypeptide in a formulation of the invention. As described previously, the chemical and physical properties, formulation considerations and methodology applicable to antibodies and functional fragments thereof, are similarly applicable to biopharmaceuticals including other polypeptide biopharmaceuticals.

Target-specific monoclonal antibodies for use as a polypeptide of the invention, or functional fragments thereof, can be produced in any of the various antibody forms and/or can be altered or modified in any of the various ways as described previously while still maintaining their specific target binding activity. Any of such antibody forms, alterations or modifications, including combinations thereof, of a target-specific monoclonal antibody, or functional fragment thereof, is included within the invention as a polypeptide. Any of such various antibody forms, alterations or modifications of a target-specific monoclonal antibody for use as a polypeptide of the invention, or a functional fragment thereof, can similarly be used in the methods, compositions and/or articles of manufacture of the invention as they are described herein. For example, target-specific monoclonal antibodies of the invention, or functional fragments thereof, include target-specific grafted, humanized, Fd, Fv, Fab, F(ab)$_2$, scFv and peptibody monoclonal antibodies as well as all other forms, alterations and/or modifications described previously, and including other forms well known to those skilled in the art.

Methods for producing hybridomas and screening for target-specific monoclonal antibodies using hybridoma technology are routine and well known in the art. For example, mice can be immunized with a target molecule such as a polypeptide and once an immune response is detected, e.g., antibodies specific for the target molecule are detected in the mouse serum, the mouse spleen is harvested and splenocytes isolated. The splenocytes are then fused by well known methods to any suitable myeloma cells, for example, cells from cell line SP20 available from the ATCC. Hybridomas are selected and cloned by limited dilution. The hybridoma clones are then assayed by methods known in the art for cells that secrete antibodies capable of binding a target molecule. Ascites fluid, which generally contains high levels of antibodies, can be generated by immunizing mice with positive hybridoma clones.

Additionally, recombinant expression in prokaryotic or eukaryotic hosts can be used to generate target-specific monoclonal antibodies. Recombinant expression can be utilized to produce single target-specific monoclonal antibody species, or functional fragments thereof. Alternatively, recombinant expression can be utilized to produce diverse libraries of heavy and light, or variable heavy and variable light chain combinations, and then screened for a monoclonal antibody, or functional fragment thereof, exhibiting specific binding activity to the target molecule. For example, heavy and light chains, variable heavy and light chain domains, or functional fragments thereof, can be co-expressed from nucleic acids encoding target-specific monoclonal antibodies using methods well known in the art to produce specific monoclonal antibody species. Libraries can be produced using methods well known in art from co-expressed populations of nucleic acids encoding heavy and light chains, variable heavy and light chain domains, or functional fragments thereof, and screened by affinity binding to the target molecule for identification of target-specific monoclonal antibodies. Such methods can be found described in, for example, *Antibody Engineering: A Practical Guide*, C. A. K. Borrebaeck, Ed., supra; Huse et al., *Science* 246:1275-81 (1989); Barbas et al., *Proc. Natl. Acad. Sci. USA* 88:7978-82 (1991); Kang et al., *Proc. Natl. Acad. Sci. USA* 88:4363-66 (1991); Plückthun and Skerra, supra; Felici et al., *J. Mol. Biol.* 222: 301-310 (1991); Lerner et al., *Science* 258:1313-14 (1992), and in U.S. Pat. No. 5,427,908.

Cloning of encoding nucleic acids can be accomplished using methods well known to those skilled in the art. Similarly, cloning of heavy and/or light chain repertoires of encoding nucleic acid, including $V_H$ and/or $V_L$ encoding nucleic acids also can be accomplished by methods well known to those skilled in the art. Such methods include, for example, expression cloning, hybridization screening with a complementary probe, polymerase chain reaction (PCR) using a complementary pair of primers or ligase chain reaction (LCR) using a complementary primer, reverse transcriptase PCR (RT-PCR) and the like. Such methods can be found described in, for example, Sambrook et al., *Molecular Cloning: A Laboratory Manual*, Third Ed., Cold Spring Harbor Laboratory, New York (2001) and Ansubel et al., *Current Protocols in Molecular Biology*, John Wiley and Sons, Baltimore, Md. (1999).

Encoding nucleic acids also can be obtained from any of various public databases including whole genome databases such as those operated by The National Center for Biotechnology Information (NCBI) of the National Institutes of Health (N1H). A particularly useful method of isolating either a single encoding nucleic or a repertoire of encoding nucleic acids for heavy and/or light chains, or functional fragments thereof, can be accomplished without specific knowledge of the coding region portion because primers are available or can be readily designed using conserved portions of antibody variable or constant region portions. For example, a repertoire of encoding nucleic acids can be cloned using a plurality of degenerate primers to such regions together with PCR. Such methods are well known in the art and can be found described in, for example, Huse et al., supra, and *Antibody Engineering: A Practical Guide*, C. A. K. Borrebaeck, Ed., supra. Any of the above methods as well as others known in the art, including combinations thereof, can be used to generate a target-specific monoclonal antibody for use as a polypeptide of the invention.

Therefore, the invention provides a formulation having an antibody, a functional fragment of an antibody as a therapeutic polypeptide. The formulation can include one or more divalent cations at a concentration between 5-200 mM and/or a pH less than 6.0. The therapeutic polypeptide can include a monoclonal antibody, Fd, Fv, Fab, F(ab'), F(ab)$_2$, F(ab')$_2$, single chain Fv (scFv), chimeric antibodies, diabodies, triabodies, tetrabodies, minibody or peptibody.

Concentrations of a polypeptide to be included in a formulation of the invention will vary, for example, depending on the activity of the polypeptide, the indication to be treated, mode of administration, the treatment regime and whether the formulation is intended for long term storage in either liquid or lyophilized form. Those skilled in the art will know what concentrations to use given these well known considerations and the state of the art in the pharmaceutical sciences. For example, there are more than 80 polypeptides approved for therapeutic use in the United States for a wide range of medical indications, modes of administration and treatment regimes. These approved polypeptides are exemplary of the range of polypeptide concentrations that can be used in a formulation of the invention.

Generally, a polypeptide including, for example, a therapeutic polypeptide, will be included in a formulation of the invention at a concentration from between about 1-200 mg/ml, about 10-200 mg/ml, about 20-180 mg/ml, particularly between about 30-160 mg/ml, more particularly between about 40-120 mg/ml, even more particularly between about 50-100 mg/ml or about 60-80 mg/ml. Polypeptide concentrations and/or amounts less than, greater than or in between these ranges also can be used in a formulation of the invention. For example, one or more polypeptides can be included in a formulation which constitute less than about 1.0 mg/ml. Similarly, a formulation can contain a concentration of one or more polypeptides greater than about 200 mg/ml, particularly when formulated for storage. Accordingly, a formulation of the invention can be produced that contains essentially any desired concentration or amount of one or more polypeptides including, for example, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190 or 200 mg./ml or more. Exemplified in the Example below is a formulation for a therapeutic polypeptide having a concentration of about 10 mg/ml.

A formulation of the invention also can include combinations of polypeptides in the formulation. For example, a formulation of the invention can include a single polypeptide for treatment of one or more conditions. A formulation of the invention also can include two or more different polypeptides. Use of multiple polypeptides in a formulation of the invention can be directed to, for example, the same or different indications. Similarly, multiple polypeptides can be used in a formulation of the invention to treat, for example, both a pathological condition and one or more side effects caused by the primary treatment. Multiple polypeptides also can be included in a formulation of the invention to accomplish different medical purposes including, for example, simultaneous treatment and monitoring of the progression of the pathological condition. Multiple, concurrent therapies such as those exemplified above as well as other combinations well known in the art are particularly useful for patient compliance because a single formulation can be sufficient for some or all suggested treatments and/or diagnosis. Those skilled in the art will know those polypeptides that can be admixed for a wide range of combination therapies. Similarly, a formulation of the invention also can be used with small molecule pharmaceuticals and combinations of one or more polypeptides together with one or more small molecule pharmaceuticals. Therefore, the invention provides for a formulation of the invention containing 1, 2, 3, 4, 5 or 6 or more different polypeptides as well as for one or more polypeptides combined with one or more small molecule pharmaceuticals.

A formulation of the invention also can include one or more preservatives and/or additives well known in the art. Similarly, a formulation of the invention can further be formulated into any of various know delivery formulations. For example, a formulation of the invention can include lubricating agents, emulsifying agents, suspending agents, preserving agents such as methyl- and propylhydroxy-benzoates, sweetening agents and flavoring agents. Such optional components, their chemical and functional characteristics are well known in the art. Similarly well known in the art are formulations that facilitate rapid, sustained or delayed release of the polypeptide after administration. A formulation of the invention can be produced to include these or other formulation components well known in the art.

A formulation of the invention also can be produced, for example, in states other than an aqueous liquid. For example, the formulations of the invention including, for example, formulations containing one or more divalent cations at a concentration between 5-200 mM and/or a pH less than 6.0, can be prepared, for example, as a lyophilized formulation. A lyophilized formulation will generally contain, for example, a bulking or caking agent and an amorphous stabilizer.

Once a formulation of the invention is prepared as described herein, stability of the one or more polypeptides contained within the formulation can be assessed using methods well known in the art. Several of such methods are exemplified further below in the Examples and include size exclusion chromatography and particle counting. Any of a variety of functional assays including, for example, binding activity, other biochemical activity and/or physiological activity can be assessed at two or more different time points to determine the stability of the polypeptide in the buffered formulation of the invention.

A formulation of the invention will, in general, be prepared according to pharmaceutical standards and using pharmaceutical grade reagents. Similarly, a formulation of the invention will, in general, be prepared using sterile reagents in a sterile manufacturing environment or sterilized following preparation. Sterile injectable solutions can be prepared using well known procedures in the art including, for example, by incorporating one or more polypeptides in the required amount in an acetic acid, glutamic acid or succinic acid buffer or excipient of the invention with one or a combination of formulation components described herein followed by sterilization microfiltration. In the specific embodiment of sterile powders for the preparation of sterile injectable solutions, particularly useful methods of preparation include, for example, vacuum drying and freeze-drying (lyophilization) as described previously. Such drying methods will yield a powder of the one or more polypeptides together with any additional desired components from a previously sterile-filtered solution thereof.

Administration and dosage regimens can be adjusted to provide an effective amount for an optimum therapeutic response. For example, a single bolus can be administered, several divided doses can be administered overtime or the dose can be proportionally reduced or increased as indicated by the exigencies of the therapeutic situation. It can be particularly useful to formulate a formulation of the invention for intravenous, parenteral or subcutaneous injection in a unit dosage form for ease of administration and uniformity of dosage in administering an effective amount of one or more polypeptides. Unit dosing refers to a physically discrete amount of pharmaceutical suited as unitary dosages for the subjects to be treated; each unit contains a predetermined quantity of active polypeptide calculated to produce a desired therapeutic effect.

For further exemplification, an effective amount of a polypeptide such as a therapeutic antibody, particularly panitumumab, can be administered, for example, more than once, at scheduled intervals over a period of time. In certain embodiments, a therapeutic antibody is administered over a period of at least a month or more including, for example, one, two, or three months or longer. For treating chronic conditions, long-term, sustained treatment is generally most effective. Shorter periods of administration can be sufficient when treating acute conditions including, for example, from one to six weeks. In general, a therapeutic antibody or other polypeptide is administered until the patient manifests a medically relevant degree of improvement over baseline for the chosen indicator or indicators.

Depending on the selected polypeptide and indication to be treated, a therapeutically effective amount is sufficient to cause a reduction in at least one symptom of the targeted pathological condition by at least about 5%, 10%, 15%, 20%, 25%, 30%, 35%, 40%, 45%, 50%, 55% or 60% or more, relative to untreated subjects. The ability of a formulation to reduce or inhibit a symptom can be evaluated, for example, in an animal model system predictive of efficacy for the targeted condition in human. Alternatively, the ability of a formulation to reduce or inhibit a symptom can be evaluated, for example, by examining an in vitro function or activity of the formulation indicative of in vivo therapeutic activity.

Actual dosage levels of one or more polypeptides in a formulation of the invention can be varied so as to obtain an amount of the active polypeptide which is effective to achieve the desired therapeutic response for a particular patient, formulation, and mode of administration, without being toxic to the patient. One skilled in the art would be able to determine administered amounts based on factors such as the subject's size, the severity of the subject's symptoms, and the selected polypeptide and/or route of administration. The selected dosage level can depend, for example, upon a variety of pharmacokinetic factors including the activity of the polypeptide employed, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts. Particular embodiments of the present invention involve administering a therapeutic polypeptide such as an antibody, or functional fragment thereof, in a formulation of the invention at a dosage of from about 1 ng of antibody per kg of subject's weight per day (1 ng/kg/day) to about 10 mg/kg/day, more particularly from about 500 ng/kg/day to about 5 mg/kg/day, and even more particularly from about 5 µg/kg/day to about 2 mg/kg/day, to a subject.

A physician or veterinarian having skill in the art can readily determine and prescribe the effective amount of the required pharmaceutical formulation. For example, the physician or veterinarian can initiate doses of a formulation of the invention at levels lower than that required in order to achieve the desired therapeutic effect and gradually increase the dosage until the desired effect is achieved. In general, a suitable daily dose of a formulation of the invention will be that amount of the polypeptide which is the lowest dose effective to produce a therapeutic effect. Such an effective amount will generally depend upon the factors described previously. It is particularly useful that administration be intravenous, intramuscular, intraperitoneal, or subcutaneous. If desired, the effective daily dose to achieve an effective amount of a formulation can be administered as two, three, four, five, six or more sub-doses administered separately at appropriate intervals throughout the day, optionally, in unit dosing amounts.

A formulation of the invention can be administered, for example, with medical devices known in the art. For example, in a particularly useful embodiment, a formulation of the invention can be administered with a needleless hypodermic injection device, such as the devices described in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which describes an implantable micro-infusion pump for dispensing medication at a controlled rate; U.S. Pat. No. 4,486,194, which describes a therapeutic device for administering medicants through the skin; U.S. Pat. No. 4,447,233, which describes a medication infusion pump for delivering medication at a precise infusion rate; U.S. Pat. No. 4,447,224, which describes a variable flow implantable infusion apparatus for continuous drug delivery; U.S. Pat. No. 4,439,196, which describes an osmotic drug delivery system having multi-chamber compartments, and U.S. Pat. No. 4,475,916, which describes an osmotic drug delivery system. Many other such implants, delivery systems, and modules are known to those skilled in the art.

In certain specific embodiments, a polypeptide for use in a formulation of the invention can additionally be formulated to facilitate selective distribution in vivo. For example, the blood-brain barrier (BBB) excludes many highly hydrophilic compounds. To facilitate crossing of the BBB if desired, a formulation can additionally include, for example, liposomes for encapsulation of one or more polypeptides. For methods of manufacturing liposomes, see, for example, U.S. Pat. Nos. 4,522,811; 5,374,548; and 5,399,331. The liposomes can further contain one or more moieties which are selectively transported into specific cells or organs, thus enhancing targeted delivery of a selected polypeptide (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180) or surfactant protein A receptor (Briscoe et al. (1995) *Am. J. Physiol.* 1233:134).

Therefore, the invention additionally provides a method of preparing a formulation. The method includes combining an aqueous solution having a buffer having a pH from about 4.0 to about 7.5 and an excipient selected from a sugar or polyol with an effective amount of a therapeutic polypeptide including, for example, an EGFR specific antibody. The method also can include one or more divalent cations at a concentration between 5-200 mM and/or be formulated a pH less than 6.0. The buffer component can include acetic acid, glutamic acid, succinic acid or priopionic acid, or salt thereof. The EGFR specific antibody can be, for example, panitumumab. One or more of the formulation components described herein can be combined with one or more effective amounts of a polypeptide to produce a wide range of formulations of the invention.

The invention further provides a method of stabilizing a polypeptide. The method includes contacting a therapeutic polypeptide with a concentration of divalent cation between about 5-150 150 mM in a buffer having a pH less than 6.0 and an excipient comprising a sugar or polyol.

One or more divalent cations, or a salt form thereof, can added to a polypeptide containing Asp or Asn to maintain or enhance stability of that polypeptide by reducing the rate or extent of isomerization and isoaspartic acid formation. The one or more divalent cations, or salt form thereof, useful for stabilizing an Asp- or Asn-containing polypeptide include any of those previously exemplified as well as other divalent cations known in the art. Similarly, as with the formulations and method of preparing a formulation of the invention, combinations of divalent cations also can be included to reduce the rate or extent of Asp or Asn isomerization. For example, combinations of two, three or more of, for example, $Ca^{+2}$, $Zn^{+2}$, $Mn^{+2}$ and/or $Mg^{+2}$ can be used to stabilize a polypeptide containing Asp, containing Asn, containing Asp and Asn or containing any of the previously described motifs or structures rendering a polypeptide susceptible to isoaspartic acid formation. Inclusion of one or more divalent cations at a concentration of between about 5-200 mM will prevent or slow Asp or Asn isomerization. Other useful divalent cation concentrations include those exemplified previously. Similarly, one or more divalent cations can be employed in the method of stabilizing a polypeptide by contacting a polypeptide in a formulation containing any combination of the constituents, components or pH values described previously or exemplified herein with one or more divalent cations between about 5-200 mM.

Additionally provided is a container containing a formulation including an aqueous solution having between about 1-10 mM acetic acid, glutamic acid, succinic acid or other buffer with a pH from about 4.0 to about 7.0, glycerol or sorbitol between about 1-10%, polysorbate 80 between about 0.001-0.010% and an effective amount of a therapeutic antibody, including, for example, an EGFR specific antibody or panitumumab. The container also can include a formulation containing the above components and one or more divalent cations at a concentration between 5-200 mM and/or be formulated a pH less than 6.0. Briefly, with respect to compositions, kits and/or medicaments of the invention, the combined effective amounts of one or more polypeptides within a formulation of the invention can be included within a single container or container means, or included within distinct containers or container means. Imaging components can optionally be included and the packaging also can include written or web-accessible instructions for using the formulation. A container or container means includes, for example, a vial, bottle, syringe or any of a variety of formats well known in the art for multi-dispenser packaging.

It is understood that modifications which do not substantially affect the activity of the various embodiments of this invention are also included within the definition of the invention provided herein. Accordingly, the following examples are intended to illustrate but not limit the present invention.

EXAMPLE I

Polypeptide Stability Characterization in Buffered Solutions

This Example describes the characterization of various formulations on the stability of panitumumab. Also described is the characterization of various formulations on the long term stability of panitumumab bulk preparations.

A variety of formulation conditions that stabilize monoclonal IgG2 antibody panitumumab are described below. These formulation conditions include those applicable for administration of the therapeutic polypeptide as well as for the storage, maintenance and/or lot preparation of the therapeutic polypeptide. The formulation conditions of the invention exemplified below confer particularly useful panitumumab stability against aggregation, chemical degradation and particle formation. These conditions were shown to be particularly effective in preventing particle formation which allows elimination of any need for in-line filter for intravenous administration.

Briefly, panitumumab was found to be stable at a pH ranging from about 5.0 to 7.0. Optimal stability was observed at a pH of 5.0 with respect to aggregation and particle formation. Formulations with a pH of 5.0 also were the clearest (ie, most transparent) liquid solution, indicating less aggregation. Particularly useful buffer systems included acetic acid, L-glutamic acid and succinic acid. All three of these buffer systems worked well near a pH of about 5.0 (e.g., from about 4.8 to about 5.2). Among these buffer systems, L-glutamic acid was observed to be equally effective or better than acetic acid for panitumumab stability. Particularly useful excipients for panitumumab included glycerol, sucrose, trehalose and sorbitol. All showed effective stabilizing properties with respect to aggregation and/or particle formation. Optimal excipients, included glycerol and sucrose.

The results set forth below show a variety of formulations that maintain, augment or optimize panitumumab stability. In certain specific formulations, particularly useful liquid formulations for panitumumab included 10 mM acetic acid, 2.6% glycerol, 0.004% polysorbate 80 at pH 5.0 and 10 mM L-glutamic acid, 2.6% glycerol, 0.004% polysorbate 80 at pH 5.0. In other specific formulations, particularly useful long-term formulations for, for example, frozen storage, maintenance and/or lot preparation such as bulk substance preparation, included 10 mM acetic acid, 2.6% glycerol at pH 5.0 and 10 mM L-glutamic acid, 2.6% glycerol at pH 5.0 when the panitumumab formulation is maintained at −30 C or below. Glycerol, sucrose and trehalose were further found to be particularly useful excipients that protected panitumumab from freeze-thaw-induced aggregation and particle formation.

The studies described herein were directed to the characterization and selection of formulations that augment retention in stability of panitumumab. Based on preliminary analysis, three buffer systems were chosen for characterizing stable liquid and frozen formulations for panitumumab. These buffer systems were acetic acid, glutamic acid and succinic acid. The characterization of formulations derived from these buffer systems is exemplified below.

One initial characterization was the visual appearance of panitumumab in various acetic acid buffer formulations. Briefly, the seven formulations listed below were assessed at different pH values.

1. pH 5.0: 20 mg/ml panitumumab, 5 mM Acetate, 5 mM Phosphate, 5% Sorbitol, pH 5.0

2. pH 5.5: 20 mg/ml panitumumab, 5 mM Acetate, 5 mM Phosphate, 5% Sorbitol, pH 5.5
3. pH 6.0: 20 mg/ml panitumumab, 5 mM Acetate, 5 mM Phosphate, 5% Sorbitol, pH 6.0
4. pH 6.5: 20 mg/ml panitumumab, 5 mM Acetate, 5 mM Phosphate, 5% Sorbitol, pH 6.5
5. pH 7.0: 20 mg/ml panitumumab, 5 mM Acetate, 5 mM Phosphate, 5% Sorbitol, pH 7.0
6. pH 7.5: 20 mg/ml panitumumab, 5 mM Acetate, 5 mM Phosphate, 5% Sorbitol, pH 7.5
7. A58N: 20 mg/ml panitumumab, 50 mM Acetate, 100 mM NaCl, pH 5.8 (control)

The visual appearance of panitumumab formulated at the above pH values ranging from 5.0 to 7.5 was assessed. The results indicated that the protein solution was clearer and more transparent at lower pH values. In comparison, formulations became more turbid at higher pH values.

Accelerated stability studies were performed to characterize the stability of panitumumab under different pH conditions. Briefly, accelerated stability studies performed at a particular pH and at, for example, 37 C in glass vials. Samples were dialyzed into the respective formulations to be tested and sterile filtered into sterile containers. Approximately 2-mL quantities of each formulated sample were placed in sterile 3-mL glass vials in a sterile hood and stoppered. Samples designated for freezing were placed in sterile polypropylene eppindorf tubes. All vials were labeled and crimped followed by placement into boxes specified for storage at −80 C, 2-8 C, and 37 C conditions. Samples were removed and analyzed at designated timepoints. Size exclusion chromatography (SEC) was used as one of the analytical methods. A TosoHaas G3000SWxl dual column in tandem was used to carry out the analysis using a mobile phase consisting of 100 mM phosphate (pH 7), 150 mM NaCl Different forms of the samples could be quantitatively evaluated and separated based on their hydrodynamic volume. Exemplary results are illustrated in FIG. 1 and show the percent monomer of panitumumab stored at 37 C for up to 2 months. Higher monomer losses were observed at higher pH conditions. The formulations exemplified in FIG. 1 at each time point were the same as those studied above with respect to visual appearance and are labeled as follows in the Figure:
1. EGF_20pH 5.0: 20 mg/ml panitumumab, 5 mM Acetate, 5 mM Phosphate, 5% Sorbitol, pH 5.0
2. EGF_20pH 5.5: 20 mg/ml panitumumab, 5 mM Acetate, 5 mM Phosphate, 5% Sorbitol, pH 5.5
3. EGF_20pH 6.0: 20 mg/ml panitumumab, 5 mM Acetate, 5 mM Phosphate, 5% Sorbitol, pH 6.0
4. EGF_20pH 6.5: 20 mg/ml panitumumab, 5 mM Acetate, 5 mM Phosphate, 5% Sorbitol, pH 6.5
5. EGF_20pH 7.0: 20 mg/ml panitumumab, 5 mM Acetate, 5 mM Phosphate, 5% Sorbitol, pH 7.0
6. EGF_20pH 7.5: 20 mg/ml panitumumab, 5 mM Acetate, 5 mM Phosphate, 5% Sorbitol, pH 7.5
7. EGF_20pH A58N: 20 mg/ml panitumumab, 50 mM Acetate, 100 mM NaCl, pH 5.8 (control)

Changes in charge variance of the above seven protein solutions also were determined by cation exchange chromatography (CEX) for the samples stored above for up to 2 months. Briefly, panitumumab was evaluated using cation exchange procedures known in the art. This method separated predominant C-terminal lysine isoforms based on protein surface charge differences using a linear salt gradient at pH 6.2 and a Dionex weak-cation exchange column (WCX-10; Sunnyvale, Calif.) and also acidic modification of some amino acids represented by deamidation.

Figure 2:
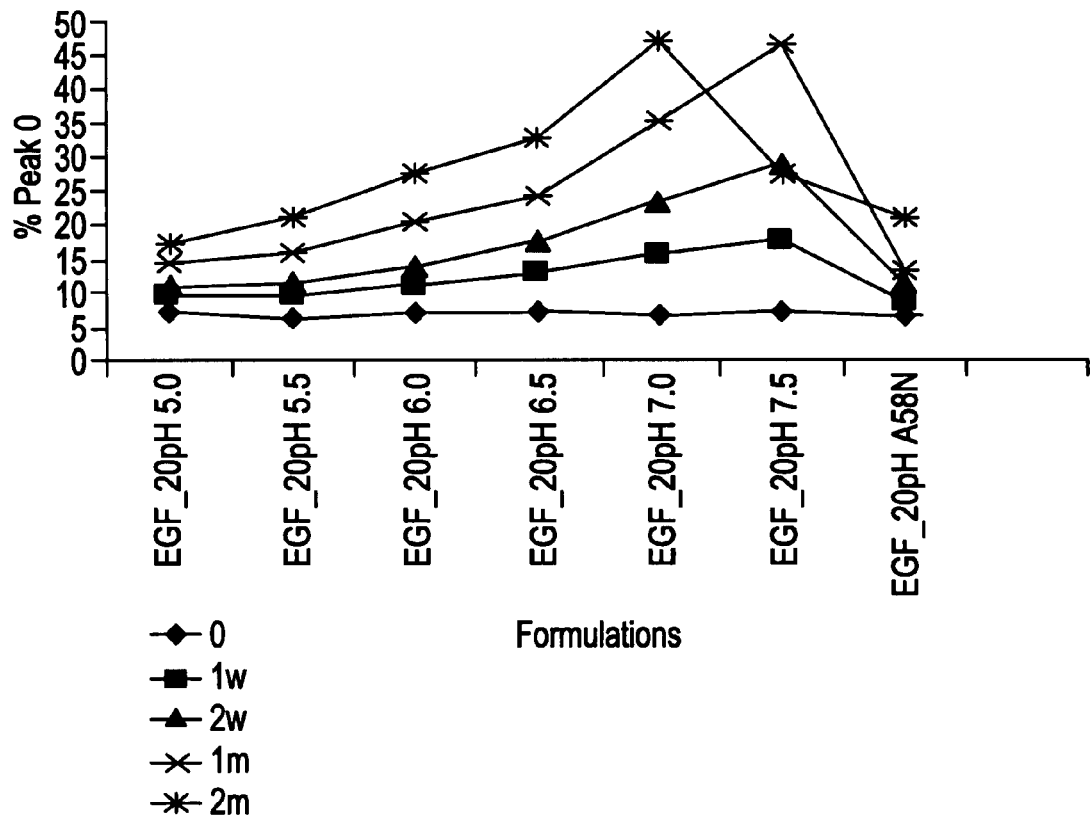
FIG. 2 shows the cation exchange chromatography results of an antibody formulated at various pH after storage at 37° C. for up to 2 months. Storage conditions corresponded to no storage (0, diamonds); 1 week (1 w, squares); 2 weeks (2 w, triangles); 1 month (1 m, X), and 2 months (2 m, stars).

CEX data for the above-described seven formulations having different pH conditions and being stored for up to 2 months at 37 C are presented in FIG. 2 (e.g., EGF_20 pH 5.0-7.5 and A58N). The result shows that the percentage of acid variants (represented by peak 0, which indicates deamidation products) is minimal at acidic pH (5.0 and 5.5).

One characteristic relating to monoclonal antibodies and other polypeptides is the occurrence of subvisible insoluble particles. In this context, a polypeptide particle refers to, for example, a fragment or aggregate of the polypeptide and can be soluble and/or insoluble. Additionally, particles can be made up of matter that is foreign (i.e., shards of glass, lint, small pieces of rubber stopper) and not necessarily composed of the polypeptide. Soluble aggregates/particles can be evaluated using methods such as SEC, for example. Particles that are insoluble can be evaluated using such methods as liquid particle counting or light obscuration approach such as HIAC, for example. Coarse particles are generally classified as particles having sizes greater than 1.0 µm and those considered fine particles are smaller in size. Using the LD-400 laser system with the HIAC instrument (Geneva, Switzerland), particle sizes between 2 and 400 µm can be measured.

Formation of insoluble particles also was assessed for above-described seven exemplary formulations assessing different pH conditions using liquid particle counting. For reference, these formulations as they are denoted in FIG. 3 were:
1. pH 5.0: 20 mg/ml panitumumab in 5 mM Acetate, 5 mM Phosphate, 5% Sorbitol, pH 5.0
2. pH 5.5: 20 mg/ml panitumumab in 5 mM Acetate, 5 mM Phosphate, 5% Sorbitol, pH 5.5
3. pH 6.0: 20 mg/ml panitumumab in 5 mM Acetate, 5 mM Phosphate, 5% Sorbitol, pH 6.0
4. pH 6.5: 20 mg/ml panitumumab in 5 mM Acetate, 5 mM Phosphate, 5% Sorbitol, pH 6.5
5. pH 7.0: 20 mg/ml panitumumab in 5 mM Acetate, 5 mM Phosphate, 5% Sorbitol, pH 7.0
6. pH 7.5: 20 mg/ml panitumumab in 5 mM Acetate, 5 mM Phosphate, 5% Sorbitol, pH 7.5
7. A58N: 20 mg/ml panitumumab in 50 mM Acetate, 100 mM NaCl, pH 5.8 (control)

The HIAC particle counter instrument was equipped with PharmSpec software version 1.4, required to measure the 10 µm and 25 µm particles present in a given Emab sample. The employed methods followed procedures complying with USP requirements of particle assessment and quality. Filtered water (0.22 micron) was drawn through a stainless steal tube using 1.0 mL volumes and flushed approximately 10 times between sample measurements. Duke scientific EZY-CAL liquid particle 10 µm size standard was used to verify proper calibration of the instrument. Both sample and standard measurements were taken with a volume of 0.2 mL, drawn 4 times, discarding the first run and averaging the last two or three. The samples were drawn from their original vials, with a slight swirl given to each sample prior to measurement to ensure uniform mixing of the solution. The standard was vigorously shaken prior to measurement.

Figure 3:
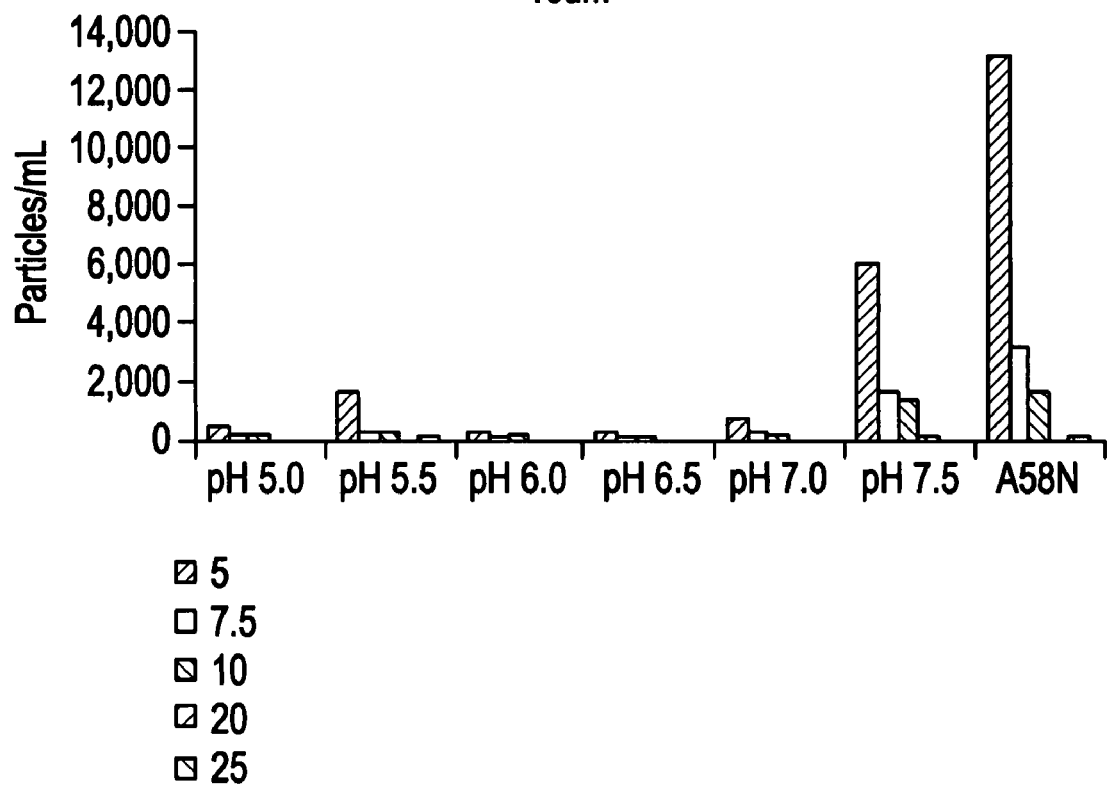
FIG. 3 shows the particle counts of an antibody formulated at various pH's after vortexing for 15 minutes at 4° C. Histogram sets for each indicated particle size correspond from left to right to 5 μm (5); 7.5 μm (7.5); 10 μm (10); 20 μm (20), and 25 μm (25).

The results of the HIAC particle counts of panitumumab formulated at various pHs after vortexing for 15 minutes at 4 C are shown in FIG. 3. Particles ranging from 5 µm to 25 µm in size were counted. The results show that all samples formulated at pH from 5.0 to 7.0 exhibited lower particle counts than those formulated at pH 7.5. Particle counts formulated in the buffer containing sodium chloride (A58N) were significantly higher than those formulated in the sorbitol buffers.

Based on the above exemplary results, a pH of 5.0 was selected for characterization of further formulations as described below.

Size exclusion chromatography was employed as described above to assess the stability of panitumumab formulated in acetic acid buffer, succinic acid buffer or glutamic acid buffer following storage at 37 C for up to 4 months. The formulations are set forth below as follows:

1. A__2.6% Glycerol_pH5_T80: 20 mg/mL panitumumab in 10 mM acetic acid acid, 2.6% glycerol, pH 5.0, 0.004% Tween 80.
2. Succ__2.6% Glycerol_pH5_T80: 20 mg/mL panitumumab in 10 mM succinic acid, 2.6% glycerol, pH 5.0, 0.004% Tween 80.
3. Gluta__2.6Glycerol_pH5_T80: 20 mg/mL panitumumab in 10 mM L-glutamic acid, 2.6% glycerol, pH 5.0, 0.004% Tween 80.

Figure 4:
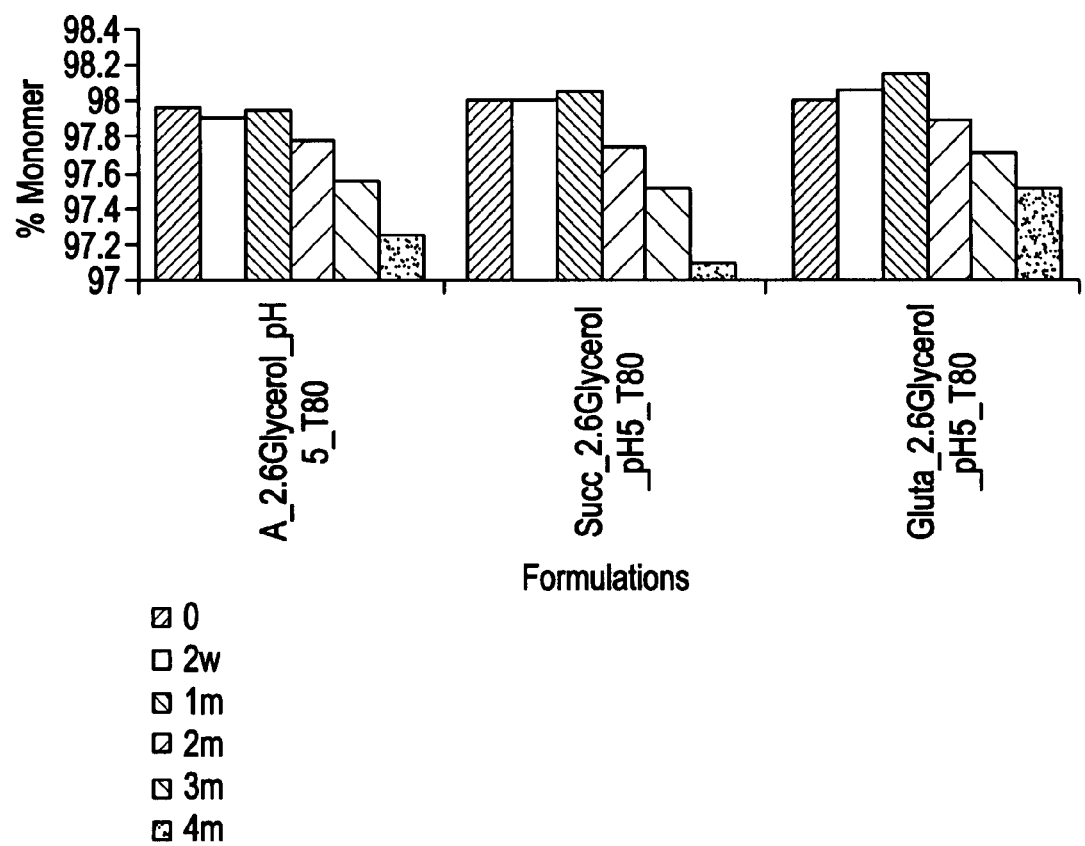
FIG. 4 shows size exclusion chromatography results of an antibody in different formulations after storage at 37° C. for up to 4 months. Histogram sets for each formulation correspond from left to right to storage periods of no storage (0); 2 weeks (2 w); 1 month (1 m); 2 months (2 m); 3 months (3 m), and 4 months (4 m).

The results of this study are shown in FIG. 4. Briefly, similar monomer content was observed for all buffer systems. The succinic acid containing formulations revealed a slightly lower monomer content and the glutamic acid containing formulation maintained the exhibited the most amount of monomer after 4 months storage at 37 C.

Stability of panitumumab formulations in any of the three acetic acid, glutamic acid or succinic acid buffers at pH 5.0 set forth above and shown in FIG. 4 also was assessed for longer periods of time and for different temperatures as described below (e.g., A__2.6% Glycerol_pH5_T80, Succ__2.6% Glycerol_pH5_T80 and Gluta__2.6Glycerol_pH5_T80). Briefly, cation exchange chromatography as described previously was employed to assess panitumumab stability in these buffer systems following incubation at 29 C for up to 6 months.

Figure 5:
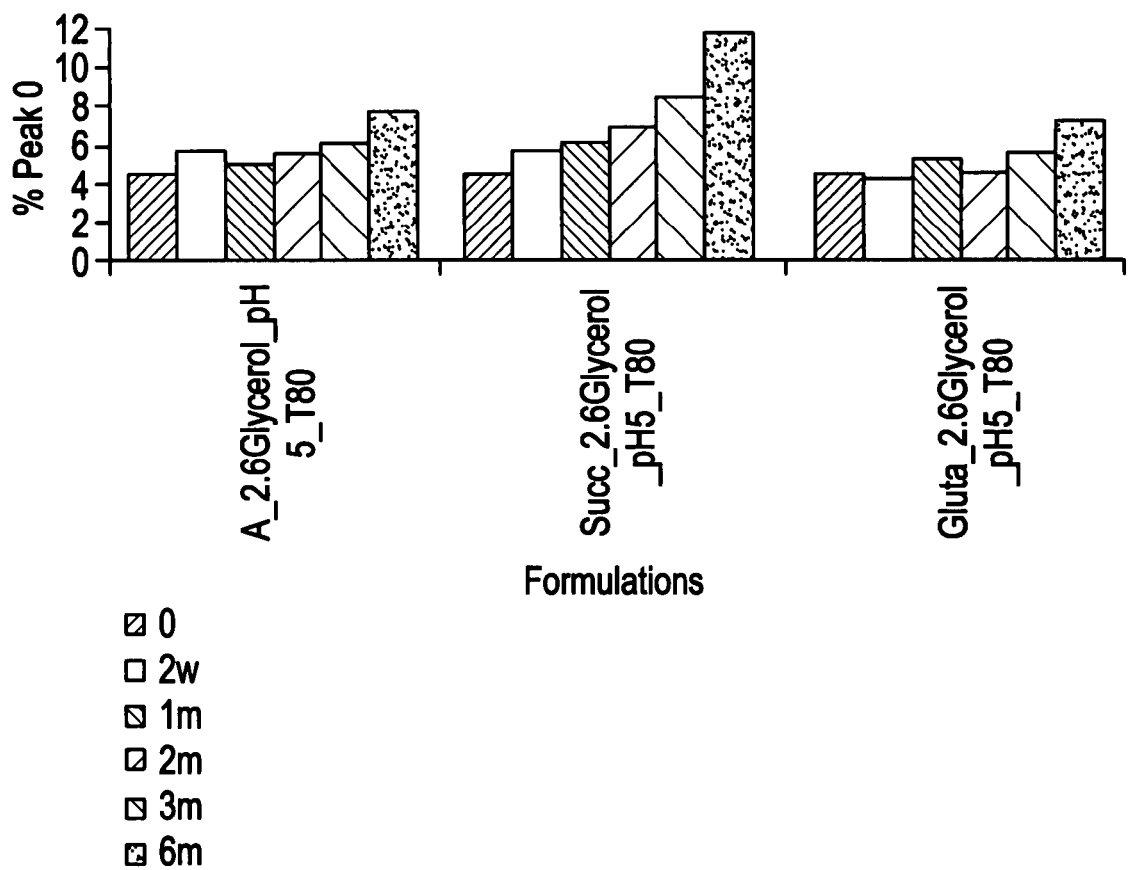
FIG. 5 shows the cation exchange chromatography of an antibody in different formulations after storage at 29° C. for up to 6 months. Histogram sets for each formulation correspond from left to right to storage periods of no storage (0); 2 weeks (2 w); 1 month (1 m); 2 months (2 m); 3 months (3 m), and 6 months (6 m).

The results are shown in FIG. 5 and indicate that the percentage of acid variants (represented by peak 0, which indicates deamidation products) is comparable in all formulations. Minimal variants formation was observed using a glutamic acid buffer system.

Particle formation of panitumumab in either acetic acid, glutamic acid or succinic acid also was assessed using HIAC particle analysis as described previously. Briefly, panitumumab was formulated as set forth below and incubated at 4 C for 6 months.

1. Ace2.6glycerolT80pH5.0: 20 mg/mL panitumumab in 10 mM acetic acid, 2.6% glycerol, pH 5.0, 0.004% Tween 80.
2. Succ2.6glycerolT80pH5.0: 20 mg/mL panitumumab in 10 mM succinic acid acid, 2.6% glycerol, pH 5.0, 0.004% Tween 80.
3. Gluta2.6glycerolT80pH5.0: 20 mg/mL panitumumab in 10 mM L-glutamic acid, 2.6% glycerol, pH 5.0, 0.004% Tween 80.

Figure 6:
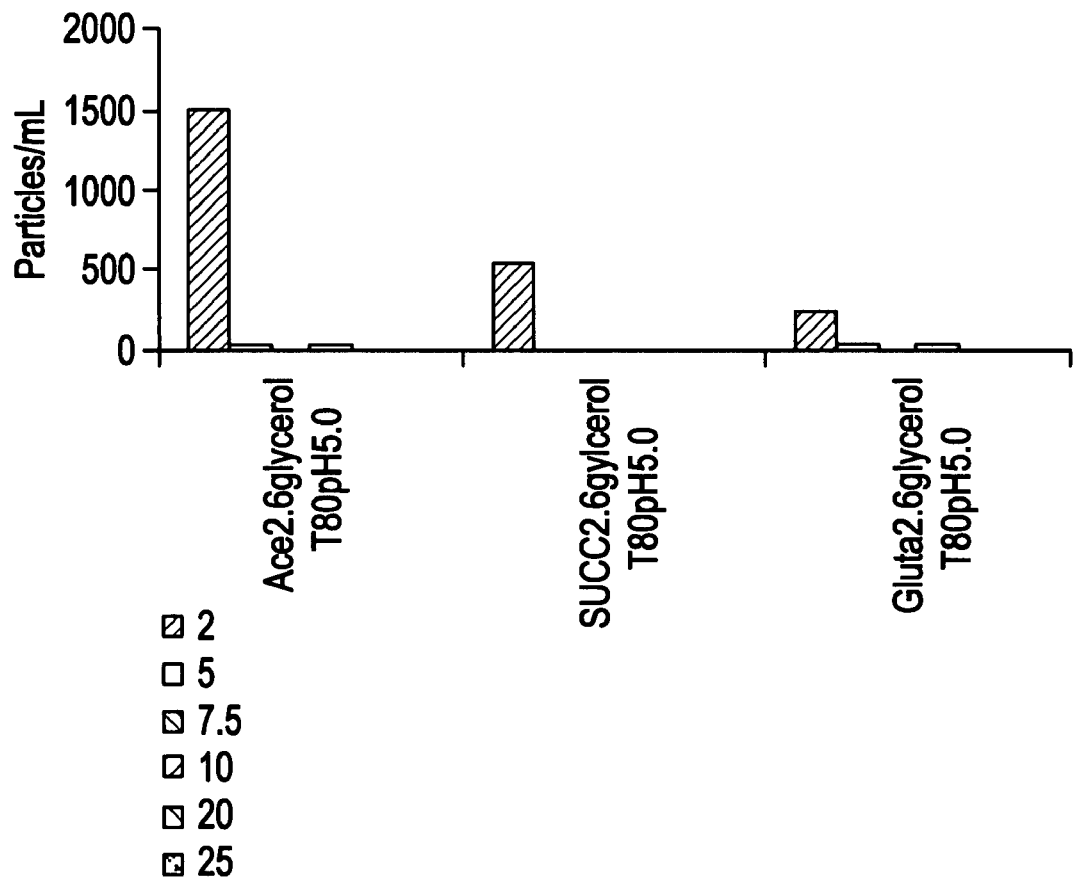
FIG. 6 shows the HIAC subvisible particle count of an antibody in different formulations following storage at 4° C. for 6 months. Histogram sets for each indicated particle size correspond from left to right to 2 μm (2); 5 μm (5); 7.5 μm (7.5); 10 μm (10); 20 μm (20), and 25 μm (25).

The result are shown in FIG. 6 and indicate acceptable particle counts in all formulations. As judged by USP guideline, there were very few particles of >10 μm and >25 μm, although particles counts of >2 μm in size in the acetate buffer was observed to be higher than those in either glutamate or succinate buffers.

Figure 7:
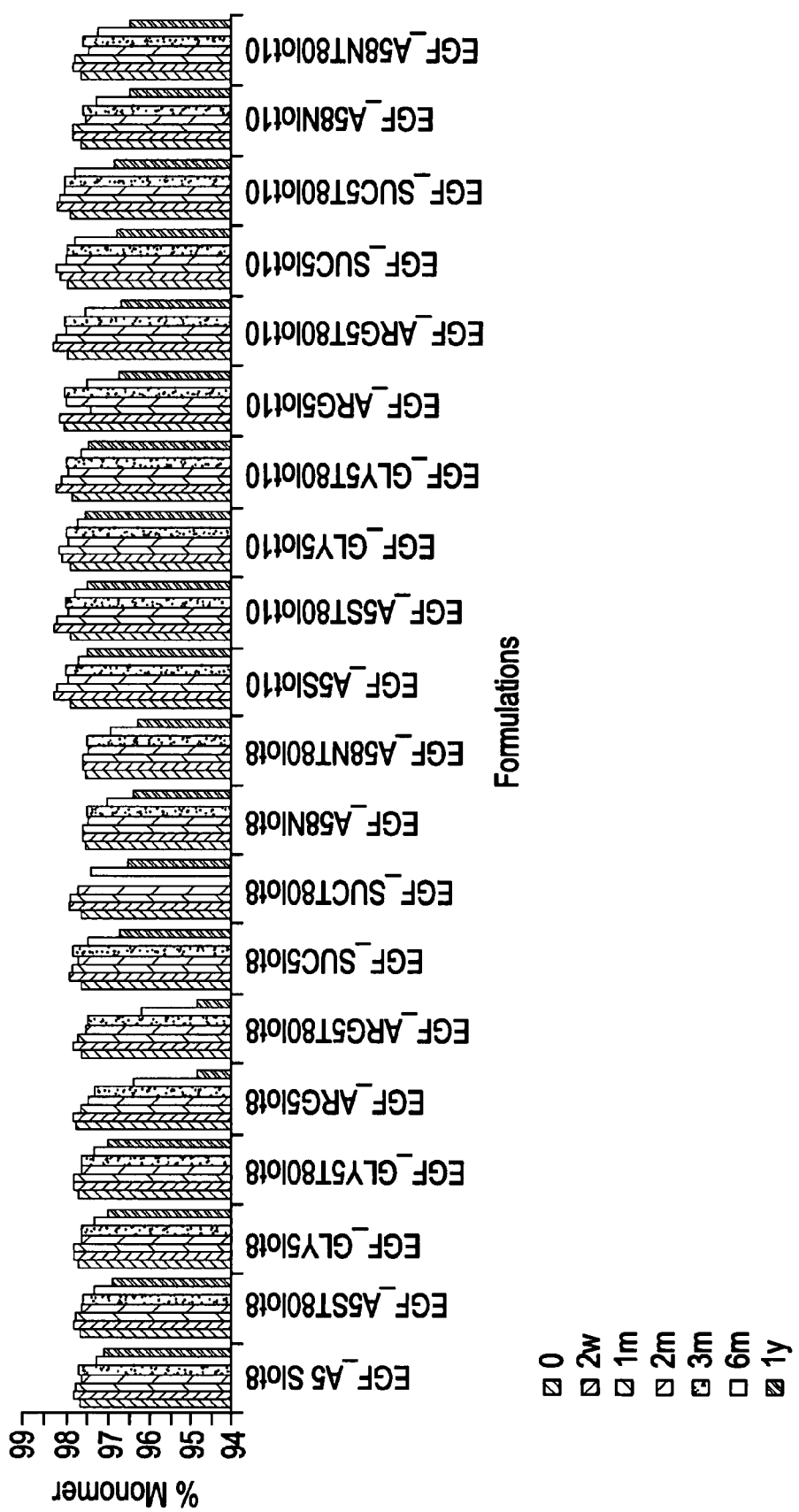
FIG. 7 shows size exchange chromatography (SEC)-HPLC measurements of antibody monomer content resulting from various formulations containing different excipients. Histogram sets for each formulation correspond from left to right to storage periods of no storage (0); 2 weeks (2 w); 1 month (1 m); 2 months (2 m); 3 months (3 m); 6 months (6 m), and 1 year (1 y).

FIG. 7 shows the monomer content as measured by SEC HPLC of various isotonic formulations containing different excipients. SEC HPLC was performed as described previously. The different excipients characterized included sorbitol (S), glycerol (GLY), arginine (ARG), sucrose (SUC) and polysorbate 80 (T80). Complete formulations for are shown below for samples stored for up to 2 years at 4 C. The result indicate that panitumumab is stable in sorbitol, glycerol, sucrose and polysorbate 80. Less stability was observed for argine.

| A5S | 10 mM NaAcetate | 5% Sorbitol | pH 5.0 | | 20 mg/mL |
|---|---|---|---|---|---|
| A5ST | 10 mM NaAcetate | 5% Sorbitol | pH 5.0 | 0.004% Tween-80 | 20 mg/mL |
| GLY5 | 10 mM NaAcetate | 2.6% Glycerol | pH 5.0 | | 20 mg/mL |
| GLY5T | 10 mM NaAcetate | 2.6% Glycerol | pH 5.0 | 0.004% Tween-80 | 20 mg/mL |
| ARG5 | 10 mM NaAcetate | 2.5% Arginine | pH 5.0 | | 20 mg/mL |
| ARG5T | 10 mM NaAcetate | 2.5% Arginine | pH 5.0 | 0.004% Tween-80 | 20 mg/mL |
| SUC5 | 10 mM NaAcetate | 9.3% Sucrose | pH 5.0 | | 20 mg/mL |
| SUC5T | 10 mM NaAcetate | 9.3% Sucrose | pH 5.0 | 0.004% Tween-80 | 20 mg/mL |
| A58N | 50 mM NaAcetate | 100 mM NaCl | pH 5.8 | | 20 mg/mL |
| A58NT | 50 mM NaAcetate | 100 mM NaCl | pH 5.8 | 0.004% Tween-80 | 20 mg/mL |

Figure 8:
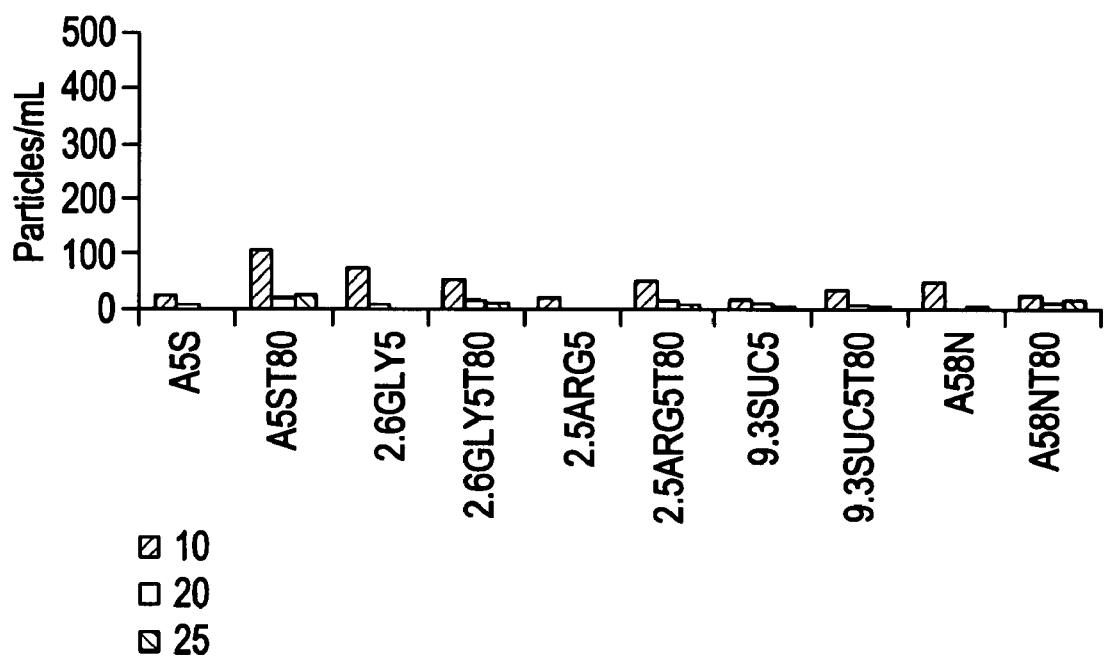
FIG. 8 shows HIAC subvisible particle measurements greater than 10 μm of different antibody formulations stored at 4° C. for 1 year. Histogram sets for each indicated particle size correspond from left to right to 10 μm (10); 20 μm (20), and 25 μm (25).

FIG. 8 shows particle count measurements for the above ten formulations having different excipients for particle sizes >10 μm using the HIAC method as described previously. The formulations and key for FIG. 8 are the same as those shown above for FIG. 7, but where GLY5 and 2.6GLY5, and GLY5T and 2.6GLY5T80, denote the same buffers between FIGS. 7 and 8, respectively. The results indicate that panitumumab is stable in a variety of formulations containing sorbitol, glycerol, sucrose and salt either in the presence or absence of polysorbate when stored for 1 year at 4 C.

In addition to the above formulations, a number of additional components and formulations were characterized for panitumumab stability under long-term storage conditions and with respect to freeze-thaw cycles. These characterizations are described further below. All assay methods were performed as described previously.

Figure 9:
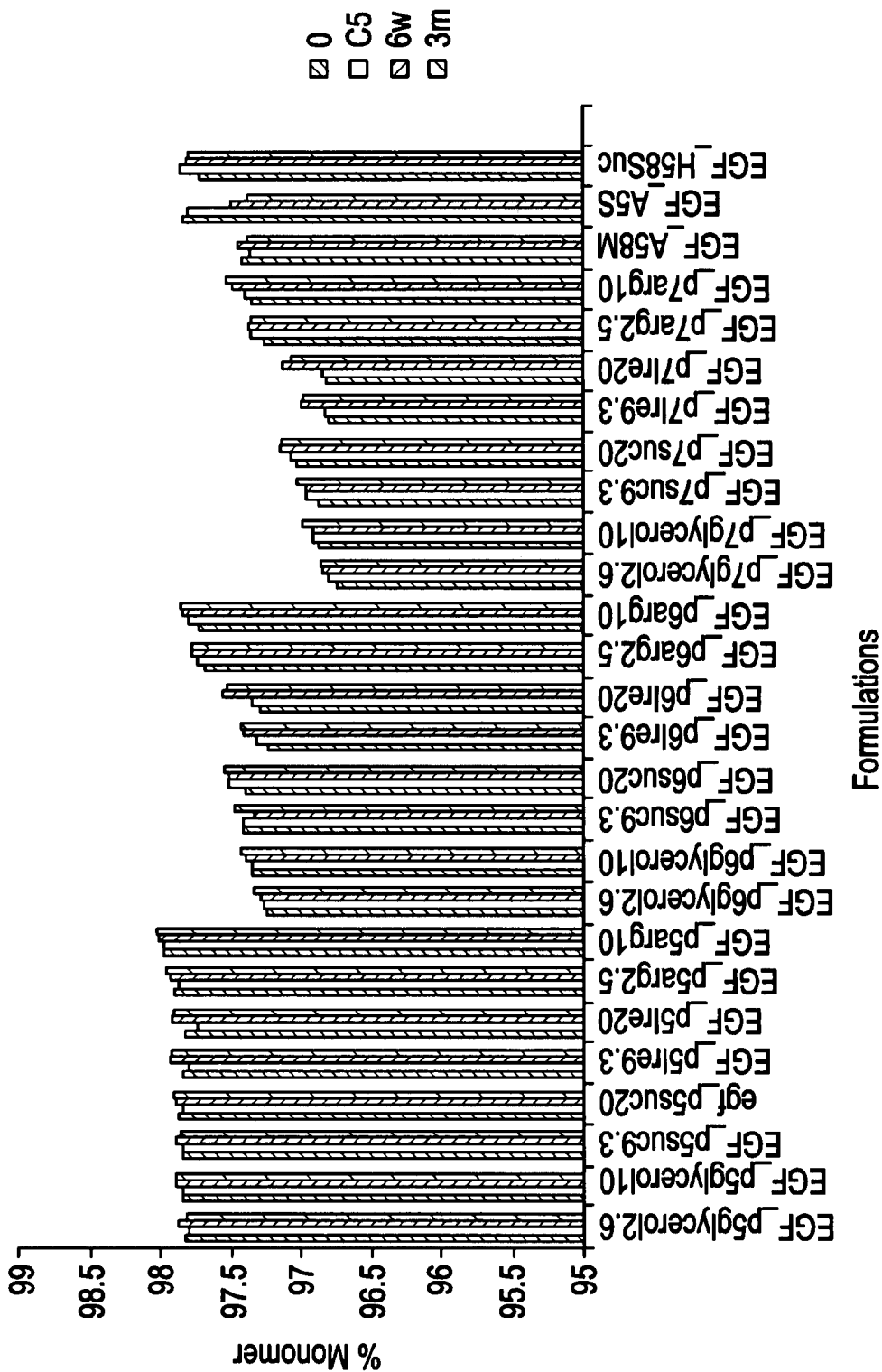
FIG. 9 shows the SE-HPLC measurements of antibody monomer content following storage at ⁻30° C. for up to 3 months in various formulations having a pH ranging from 5.0 to 7.0 and containing different excipients. Histogram sets for each formulation correspond from left to right to stress conditions and storage periods of no storage (0); 5 times freeze and thaw with no months or weeks of –30 C storage (C5); 6 weeks (6 w), and 3 months (3 m).

Briefly, FIG. 9 shows the monomer percentage of panitumumab analyzed by SE-HPLC in various formulations at a pH ranging from 5.0 to 7.0. Different excipients were included as set forth below for each formulation. The panitumumab samples were stored for up to 3 months at −30 C. These formulations were studied in relation to developing a frozen formulation or frozen drug substance or a bulk substance solution.

1. EGF_p5glycerol2.6: 40 mg/mL panitumumab in 10 mM acetate, 2.6% glycerol, pH 5.0
2. EGF_p5glycerol10: 40 mg/mL panitumumab in 10 mM acetate, 10% glycerol, pH 5.0
3. EGF_p5suc9.3: 40 mg/mL panitumumab in 10 mM acetate, 9.3% sucrose, pH 5.0
4. EGF_p5suc20: 40 mg/mL panitumumab in 10 mM acetate, 20% sucrose, pH 5.0
5. EGF_p5tre9.3: 40 mg/mL panitumumab in 10 mM acetate, 9.3% trehalose, pH 5.0
6. EGF_p5tre20: 40 mg/mL panitumumab in 10 mM acetate, 20% trehalose, pH 5.0
7. EGF_p5arg2.5: 40 mg/mL panitumumab in 10 mM acetate, 2.5% arginine, pH 5.0

8. EGF_p5arg10: 40 mg/mL panitumumab in 10 mM acetate, 10% arginine, pH 5.0
9. EGF_p6glycerol2.6: 40 mg/mL panitumumab in 10 mM potassium phosphate, 2.6% glycerol, pH 6.0
10. EGF_p6glycerol0: 40 mg/mL panitumumab in 10 mM potassium phosphate, 10% glycerol, pH 6.0
11. EGF_p6suc9.3: 40 mg/mL panitumumab in 10 mM potassium phosphate, 9.3% sucrose, pH 6.0
12. EGF_p6suc20: 40 mg/mL panitumumab in 10 mM potassium phosphate, 20% sucrose, pH 6.0
13. EGF_p6tre9.3: 40 mg/mL panitumumab in 10 mM potassium phosphate, 9.3% trehalose, pH 6.0
14. EGF_p6tre20: 40 mg/mL panitumumab in 10 mM potassium phosphate, 20% trehalose, pH 6.0
15. EGF_p6arg2.5: 40 mg/mL panitumumab in 10 mM potassium phosphate, 2.5% arginine, pH 6.0
16. EGF_p6arg10: 40 mg/mL panitumumab in 10 mM potassium phosphate, 10% arginine, pH 6.0
17. EGF_p7glycerol2.6: 40 mg/mL panitumumab in 10 mM potassium phosphate, 2.6% glycerol, pH 7.0
18. EGF_p7glycerol 10: 40 mg/mL panitumumab in 10 mM potassium phosphate, 10% glycerol, pH 7.0
19. EGF_p7suc9.3: 40 mg/mL panitumumab in 10 mM potassium phosphate, 9.3% sucrose, pH 7.0
20. EGF_p7suc20: 40 mg/mL panitumumab in 10 mM potassium phosphate, 20% sucrose, pH 7.0
21. EGF_p7tre9.3: 40 mg/mL panitumumab in 10 mM potassium phosphate, 9.3% trehalose, pH 7.0
22. EGF_p7tre20: 40 mg/mL panitumumab in 10 mM potassium phosphate, 20% trehalose, pH 7.0
23. EGF_p7arg2.5: 40 mg/mL panitumumab in 10 mM potassium phosphate, 2.5% arginine, pH 7.0
24. EGF_p7arg10: 40 mg/mL panitumumab in 10 mM potassium phosphate, 10% arginine, pH 7.0
25. EGF_A58N: 50 mM acetate, 100 mM sodium chloride, pH 5.8 (control)
26. EGF_A5S: 10 mM acetate, 5% sorbitol, pH 5.0 (control)
27. EGF_H58Suc: 50 mM histidine, 1% sucrose, pH 5.8 (control)

Figure 10:
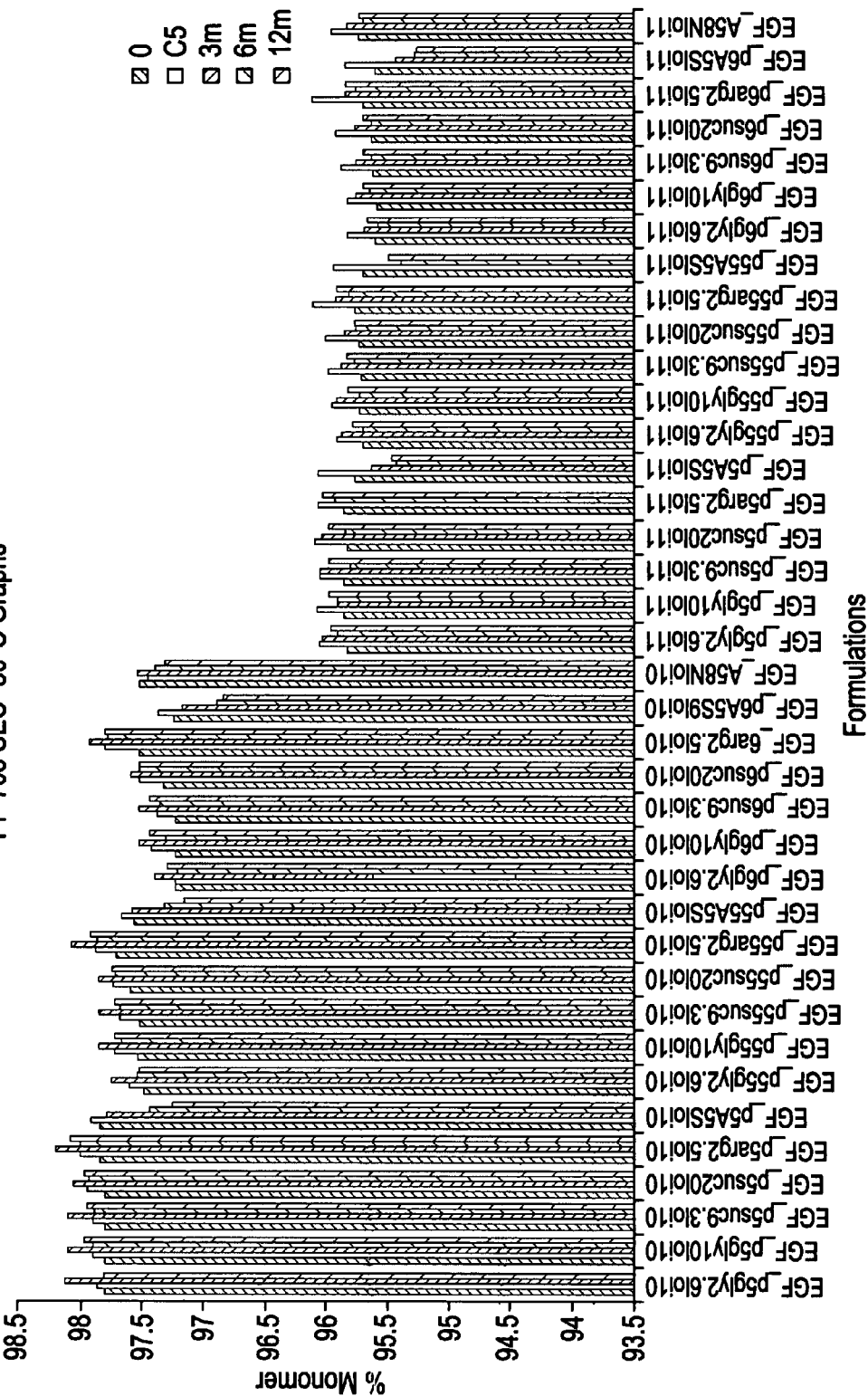
FIG. 10 shows the SE-HPLC measurements of antibody monomer content following storage at –30° C. for up to 1 year in either acetate or phosphate buffer in various formulations having a pH ranging from 5.0 to 6.0 and containing different stabilizers. Histogram sets for each formulation correspond from left to right to stress conditions and to storage periods of no storage (0); 5 times freeze and thaw with no months or weeks of –30 C storage (C5); 3 months (3 m); 6 months (6 m), and 12 months (12 m).

FIG. 10 shows the percent monomer of panitumumab analyzed by SE-HPLC as a function of pH (5 to 6) and a variety of stabilizers in either acetate or phosphate buffer. The result indicate that when panitumumab is stored at −30 C for up to one year the monomer content does not change significantly. The following formulations were characterized:
1. EGF_p5gly2.6: 10 mM Acetate, 2.6% Glycerol, pH 5.0
2. EGF_p5gly10: 10 mM Acetate, 10% Glycerol, pH 5.0
3. EGF_p5suc9: 10 mM Acetate, 9.3% Sucrose, pH 5.0
4. EGF_p5suc20: 10 mM Acetate, 20% Sucrose pH 5.0
5. EGF_p5arg2.5: 10 mM Acetate, 2.5% Arginine pH 5.0
6. EGF_p5A5S: 10 mM Acetate, 5% Sorbitol pH 5.0
7. EGF_p55gly2.6: 10 mM Acetate, 2.6% Glycerol pH 5.5
8. EGF_p55gly10: 10 mM Acetate, 10% Glycerol pH 5.5
9. EGF_p55suc9.3: 10 mM Acetate, 9.3% Sucrose pH 5.5
10. EGF_p55suc20: 10 mM Acetate, 20% Sucrose pH 5.5
11. EGF_p55arg2.5: 10 mM Acetate, 2.5% Arginine pH 5.5
12. EGF_p55A5S: 10 mM Acetate, 5% Sorbitol pH 5.5
13. EGF_p6gly2.6: 10 mM Potassium Phosphate, 2.6% Glycerol pH 6.0
14. EGF_p6gly10: 10 mM Potassium Phosphate, 10% Glycerol pH 6.0
15. EGF_p6suc9.3: 10 mM Potassium Phosphate, 9.3% Sucrose pH 6.0
16. EGF_p6suc20: 10 mM Potassium Phosphate, 20% Sucrose pH 6.0
17. EGF_p6arg2.5: 10 mM Potassium Phosphate, 2.5% Arginine pH 6.0
18. EGF_p6A5S: 10 mM Potassium Phosphate, 5% Sorbitol pH 6.0

Figure 11:
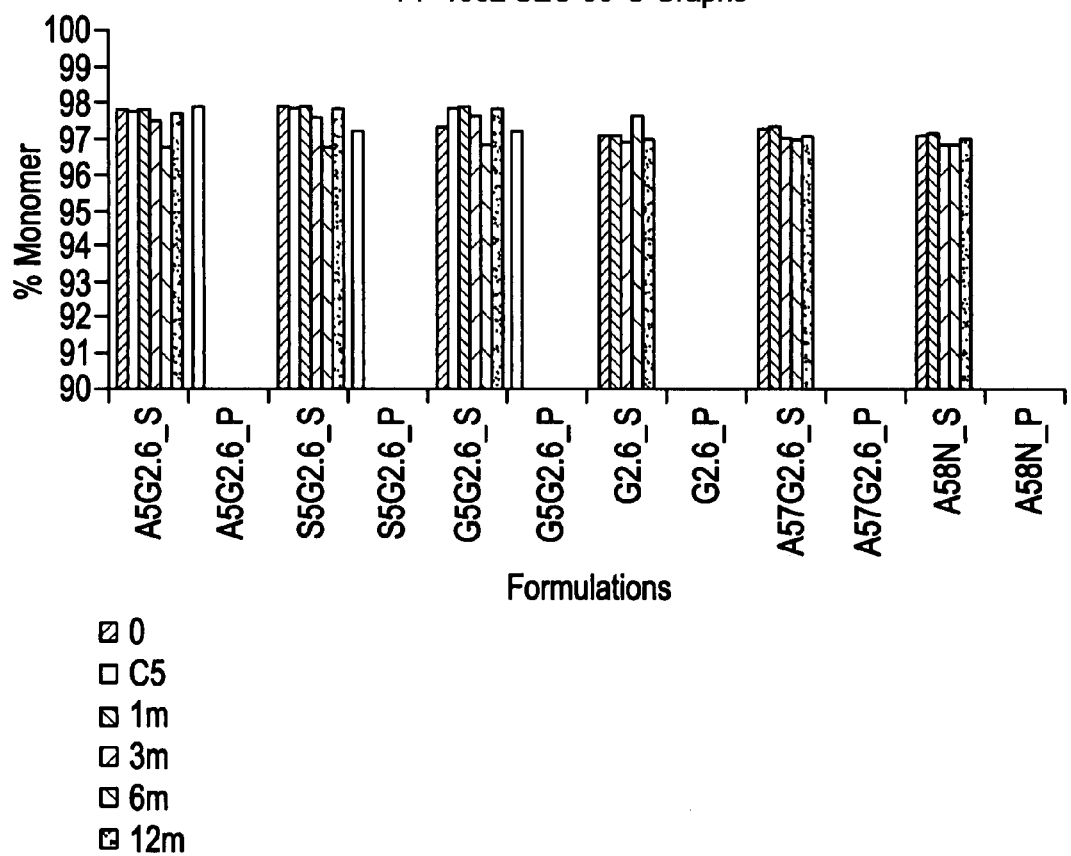
FIG. 11 shows the SE-HPLC measurements of antibody monomer content of different formulations following storage at ⁻30° C. for up to 1 year in either stainless steel or polypropylene containers. Histogram sets for each formulation correspond from left to right to stress conditions and to storage periods of no storage (0); 5 times freeze and thaw with no months or weeks of –30 C storage (C5); 1 month (1 m); 3 months (3 m); 6 months (6 m), and 12 months (12 m).

FIG. 11 shows the monomer percent of panitumumab analyzed by SE-HPLC. For this characterization, panitumumab was included at 40 mg/mL and stored at −30 C for up to one year in the various formulations listed shown below.

| Name | Buffer | Excipients | pH |
| --- | --- | --- | --- |
| A5G2.6 | 10 mM Na Acetate | 2.6% Glycerol | 5.0 |
| S5G2.6 | 10 mM Succinic acid | 2.6% Glycerol | 5.0 |
| G5G2.6 | 10 mM Glutamic acid | 2.6% Glycerol | 5.0 |
| G2.6 | No Buffering Agnet | 2.6% Glycerol | ~5.8 |
| A57G2.6 | 10 mM Acetate | 2.6% Glycerol | 5.7 |
| A58N | 50 mM Na Acetate | 100 mM NaCl | 5.8 |

The results indicate that storage at −30 C for more than 12 months did not result in any significant differences between any of the above formulations. In this study, the effect of storage in stainless steel containers (S) also was compared with storage in polypropylene (P) bottles as shown in FIG. 11. No observable differences between these two containers could be determined.

Figure 12:
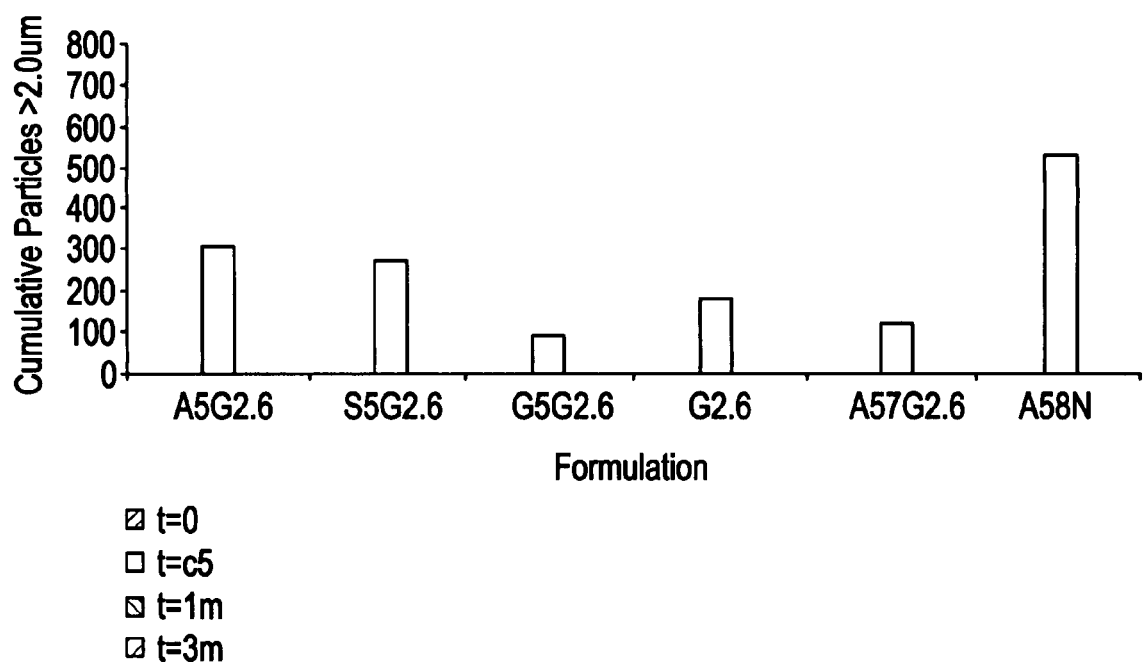
FIG. 12 shows the effect of freeze/thawing and storage at –30° C. on particle formation of various antibody formulations. Histogram sets for each formulation correspond from left to right to stress conditions and to storage periods of no storage (t=0); 5 times freeze and thaw with no months or weeks of –30 C storage (t=c5); 1 month (t=1 m), and 3 months (t=3 m).

FIG. 12 shows the effect of freeze-thaw cycles and storage at −30 C on particle formation of panitumumab in the formulations described above for FIG. 11. The results indicate acceptable particle numbers for each of the studied formulations.

EXAMPLE II

Stable Liquid Formulations Reducing Isoaspartic Acid Formation

This Example describes the use of the divalent cation calcium chloride ($CaCl_2$) to increase stability of panitumumab in a liquid formulation.

The aspartic acid residue in CDR3 of the anti-EGFR antibody panitumumab is in a flexible, solvent exposed beta-turn and was used as an exemplary polypeptide to demonstrate divalent cation inhibition of aspartic acid isomerization. This aspartyl residue also does not appear to be in network with other secondary structures and is available to interact with solvent and divalent metal ions. As described further below, inclusion of a divalent metal such as $CaCl_2$ in a polypeptide formulation slowed the succinimide intermediate kinetics and stabilized the polypeptide structure. The base formulation used to assess any effects of divalent cations on polypeptide stability was 10 mM sodium acetate, 2.6% glycerol, 0.004% polysorbate 80, pH5.0 at 20 mg/mL polypeptide and varying amounts of divalent cation as indicated below (eg, 0, 25, 50, 75, 100, 150 mM).

To assess the effect of divalent cations on the level of isoaspartyl degradation, the anti-EGFR antibody panitumumab was aged in different concentrations of $CaCl_2$. Degradation of isoaspartyl 92 of the light chain was quantified by reverse phase (RP) HPLC/UV of the reduced and alkylated antibody.

Panitumumab, an anti-EGFR IgG2 kappa monoclonal antibody, was produced and purified according to standard procedures well known in the art. The antibody was aged in buffers at pH 5.0 containing from 0-150 mM concentrations of $CaCl_2$ at both 29° C. and 37° C. for up to 3 months.

Following incubation, reduction and alkylation was performed using the antibody under denaturing conditions to produce the free heavy and light chains for further analytical characterization. Briefly, antibody was diluted to 2 mg/mL with a buffer including 7.5 M guanidine hydrochloride (catalog No. 7716, Mallinckrodt, Phillsburg, N.J., USA), 0.1 M Tris-HCl (catalog No. 93363, Sigma, St. Louis, Mo., USA), 1 mM ethylenediaminetetraacetic acid (EDTA, catalog No. 6281-92-6, Sigma) pH 7.5 to a volume of 0.5 mL. A 5 mL aliquot of a 0.5 M dithiothreitol (DTT, catalog No. D5545, Sigma) stock solution was added to obtain 5 mM DTT concentration and the reaction mixture was placed at 37° C. for 30 minutes. Polypeptide solution was then cooled to room temperature and a 13 μL aliquot of a 0.5 M iodoacetamide (IAM, catalog No. 111149, Sigma) stock solution was added to reach 13 mM IAM. The alkylation was performed at room temperature for 40 minutes while being protected from light. The 0.5 mL of buffer of the reduced and alkylated protein was exchanged with a 1 mL of 10 mM sodium acetate (catalog No. 9526-03, J. T. Baker, Philipsburg, N.J. USA) solution at pH 5.0 to a final concentration of 1 mg/mL of protein. Buffer exchange was performed using a NAP-5 gel filtration column packed with Sephadex G 26 medium (Amersham Pharmacia Biotech, Orsay, France) following the manufacturer recommendations.

Figure 14:
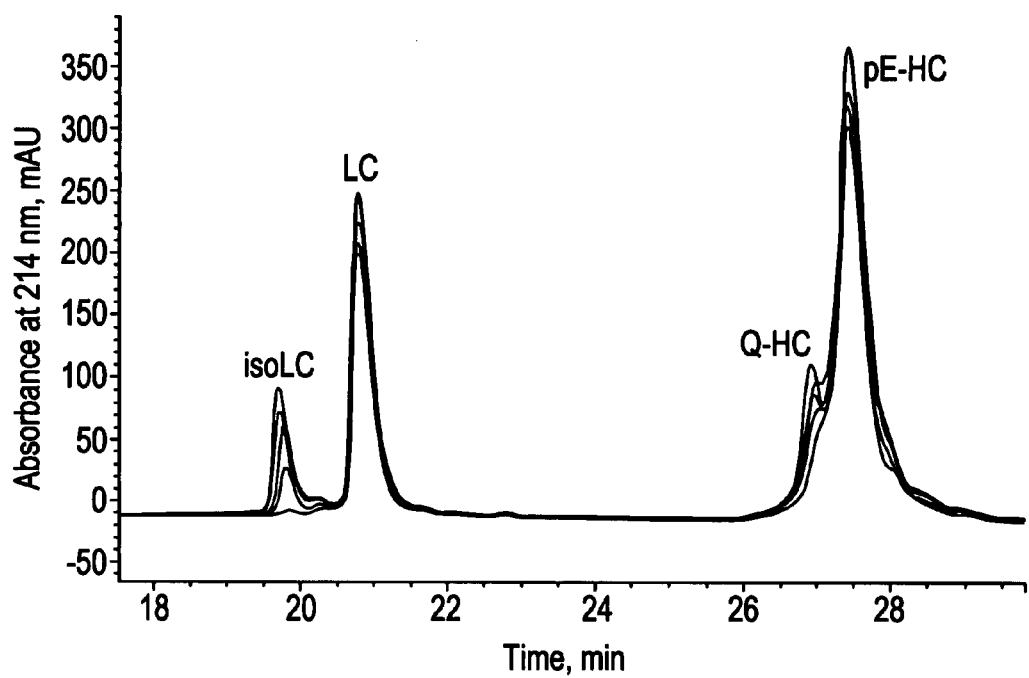
FIG. 14 shows the quantification of isoaspartyl in an antibody light chain by reversed phase chromatogram of reduced and alkylated antibody after degradation in a pH 5.0 buffer.

RP HPLC/UV chromatography was performed following reduction and alkylation. Reduction and alkylation of antibody in a pH 5.0 buffer was performed as described above. Reversed-phase HPLC/MS of the reduced and alkylated antibody was performed on an Agilent 1100 Capillary HPLC system equipped with a UV detector, autosampler, a nanoflow cell and temperature controlled column compartment (Agilent, Palo Alto, Calif., USA). The mobile phase included 0.1% aqueous trifluoroacetic acid (TFA, J. T. Baker, Phillipsburg, N.J., USA) in solvent A and 80% N-propanol (Burdick & Jackson, Muskegon, Mich., USA), 10% acetonitrile (ACN; J. T. Baker), 9.9% water with 0.1% TFA in solvent B. Agilent Zorbax SB300 CN column with 3.5 μm particle size, 300 Å pore size, 50×1 mm, was used for the HPLC/MS analysis. The column was operated at 75° C. and flow rate of 50 μL/min. The column eluate was analyzed by the UV detector and then directed to an on-line mass spectrometer. The same type of Zorbax column in 150×4.6 mm format at 1 mL/min was used for UV detection only. A linear gradient of increasing B from 18% to 26% was utilized for the separation of light and heavy chains and their variants The results of the above degradation analysis are shown in the reversed phase chromatogram of FIG. 14. Blue is a control sample that was frozen at $^-70°$ C. The remaining chromatographic traces are from samples aged at 37° C. for 1 (red), 2 (green), 3 (lavender) and 4 (brown) months. Degradations were identified as the isomerization of light chain (isoLC), increasing with time, and formation of pyroglutamic acid at the N-terminus of heavy chain (pE-HC), decreasing with time. LC corresponds to the antibody's light chain peak whereas Q-HC corresponds to the antibody's heavy chain peak.

Correlation between the percentage of isomerized light chain of isoaspartyl in position 92 also was assessed as a function of incubation time in solutions with different concentrations of $CaCl_2$ at a pH 5.0 at 37° C. Different concentrations of $CaCl_2$ were introduced in the aging solution to inhibit the isomerization of aspartyl 92 in the CDR3 region of panitumumab's light chain. Formation of isoLC was assessed as described above.

Figure 15:
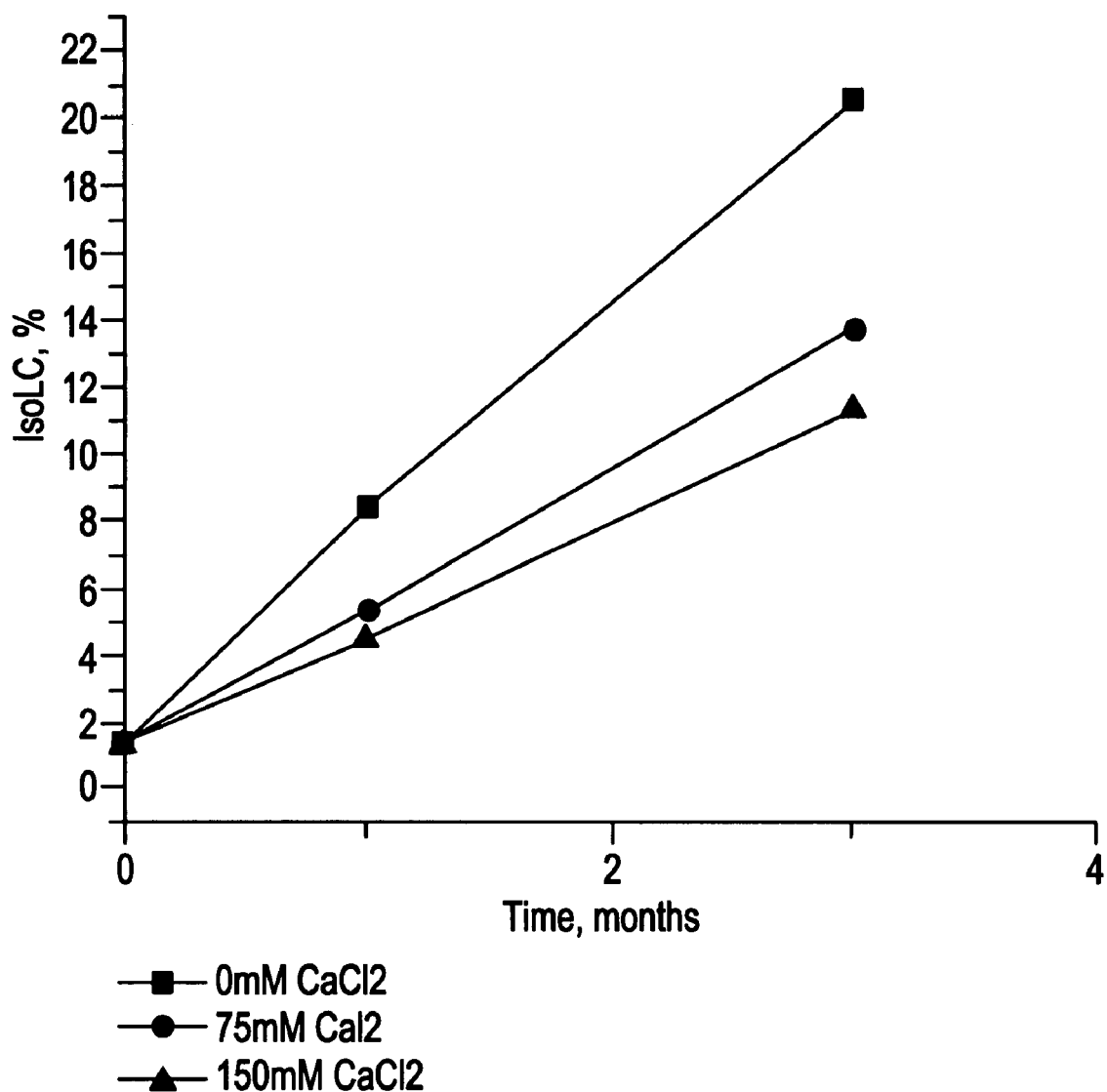
FIG. 15 shows the correlation between the percentage of isomerized light chain (isoLC) of an antibody as a function of incubation time at 37° C. in solutions with different concentrations of calcium chloride ($CaCl_2$) at pH 5.0.

The results of the above degradation time course are shown in FIG. 15 and reveal that aged samples containing 150 mM $CaCl_2$ at 37° C. for 3 months had an isoLC decrease of 10%. Incubation under these conditions without calcium ions increased the loss to 19% (see also FIG. 16C). These results indicate that in the presence of $CaCl_2$ at pH 5.0, the loss of antibody stability and potency due to the isomerization of aspartyl residue 92 was markedly slowed down.

Figure 16A:
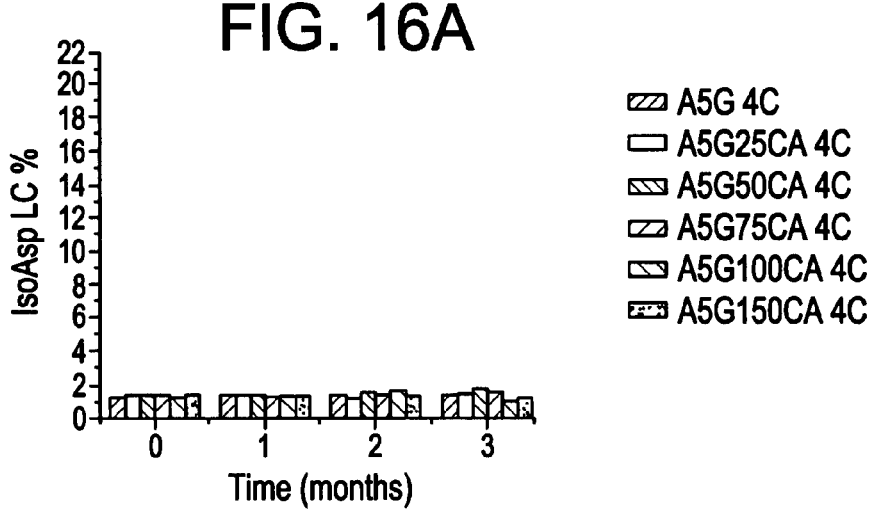
FIGS. 16A-C show the correlation between the percentage of isomerized light chain (isoLC) of an antibody containing an aspartic acid residue susceptible to isomerization as a function of incubation time at 4° C.
Figure 16B:
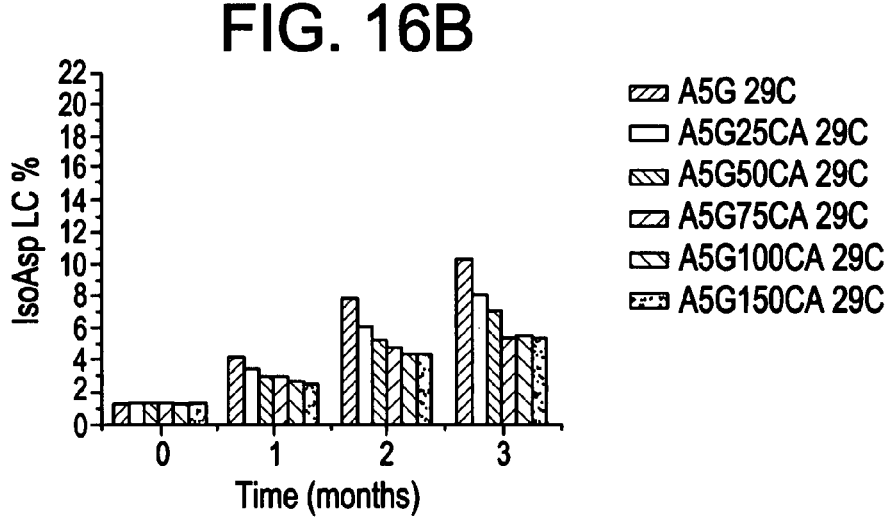
Figure 16C:
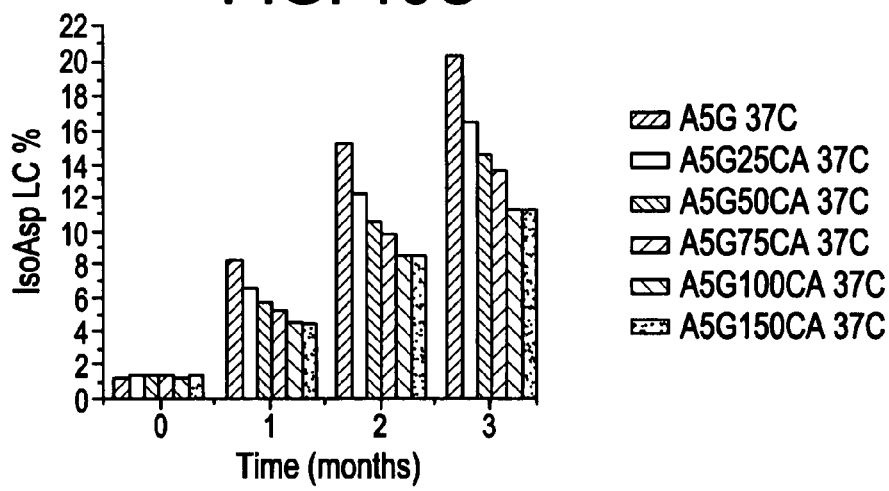

FIG. 16A-C is a further degradation time course assessing the correlation between the percentage of isoLC formation as a function of incubation time in solutions with different concentrations of $CaCl_2$ at pH 5.0 following incubation at different temperatures. As described above, different concentrations of $CaCl_2$ were introduced in the aging solution to inhibit the isomerization of aspartyl 92 and the samples were incubated at either 4° C., 29° C. or 37° C. for up to 3 months. The results indicate that at the higher temperatures addition of the amount of $CaCl_2$ added to the samples directly correlated with loss of isoLC formation and enhanced polypeptide stability.

To assess any effect on antibody activity, a cell proliferation assay of antibody potency in the presence of varying concentrations of $CaCl_2$ were performed. Briefly, the murine interleukin-3 (mIL-3) dependent cell line 32D clone 3 (ATCC CRL-11346) was modified to express the full length human EGFR. The cells were grown in RPMI 1640 with GlutaMAX™ and HEPES (Invitrogen), 10% heat inactivated fetal bovine serum (HyClone), geneticin (Invitrogen) and 5 ng/mL recombinant mIL-3 (Amgen). Assay medium was RPMI 1640 with GlutaMAX™ and HEPES, and 10% heat inactivated fetal bovine serum. For the assay, cells were washed with phosphate buffered saline and dispensed to Falcon 96 well clear plates at 20,000 cells/well. EGF at 0.85 ng/mL, control and aged samples of the anti-EGFR antibody of varying concentrations were added and incubated at 37° C. for approximately 24 hours. AlamarBlue™ (Accumed International), a redox dye that fluoresces in response to live cells, was added and the incubation continued for an additional 24 hours. Relative fluorescence was measured using a Fusion™ α (Perkin Elmer) plate reader at 530 nm excitation, 590 nm emission. A 4-parameter logistic curve-fitting program was used to determine the inhibitory concentration 50 ($IC_{50}$) of the antibody samples. The reported in-vitro potency (%) was relative to the $IC_{50}$ of the reference lot (assigned 100% potency).

The results are shown in FIG. 17 and indicate a significant protection of antibody potency loss in the presence of $CaCl_2$ compared to without divalent cation. These results further show that divalent cations can be used to retain substantially all or most of an antibody's activity since little diminution in activity was observed over a period of 2 months at either 29° C. or 37° C.

A further assessment of the reduction antibody degradation in the presence of $CaCl_2$ was performed using SE-HPLC to characterize whether the presence of divalent cations had an effect on polypeptide aggregation or dimer formation. Antibody samples were formulated in various $CaCl_2$ concentrations ranging from 0-150 mM and stored at 4° C. and 29° C. for 4 months. SE-HPLC was performed as described previously in Example I.

Figure 18A:
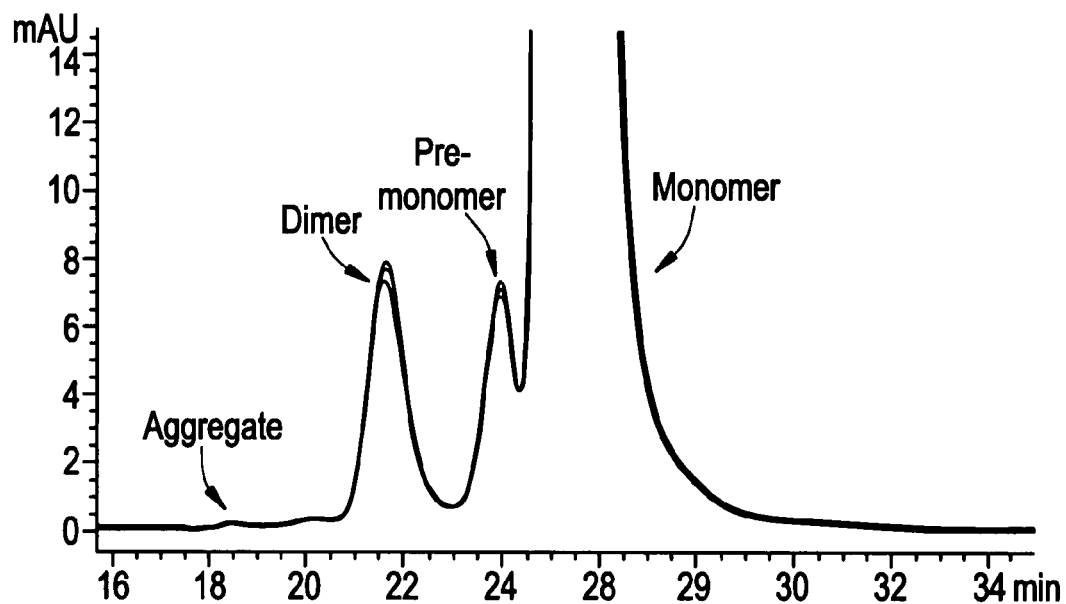
(FIG. 18A) or 29° C.
Figure 18B:
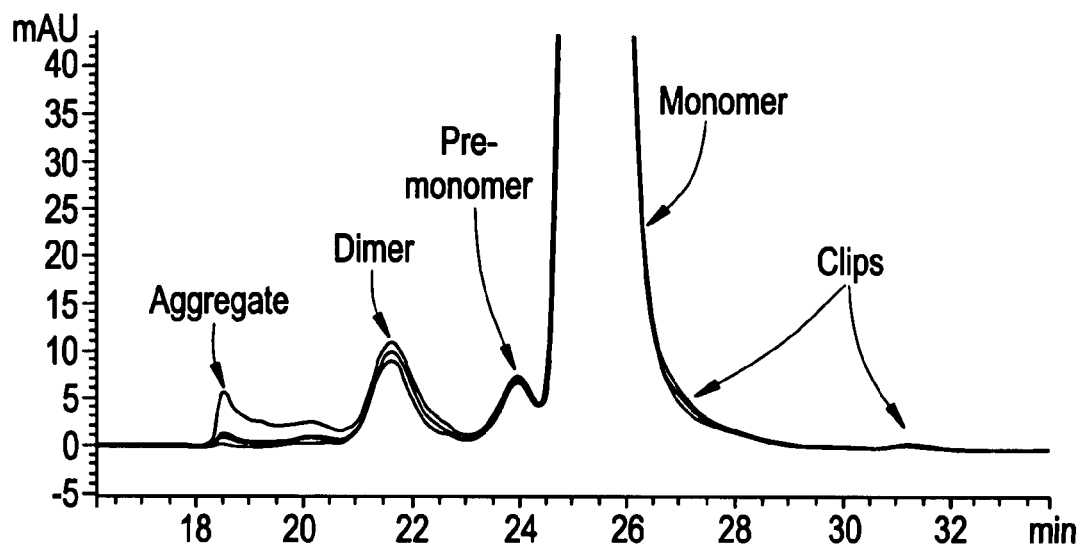
(FIG. 18B).

FIGS. 18 A and B show the SE-HPLC profiles of antibody following incubation under the above conditions. The results following incubation after 4 months at 4° C. showed no detectable increase in polypeptide aggregation or dimer formation with increasing concentrations of $CaCl_2$. The aggregates remained at 0.05% (FIG. 18A). After incubation for 4 months at 29° C., the aggregation slightly increased to 0.33% in 75 mM $CaCl_2$ solution and to 1% in 150 mM $CaCl_2$ solution (FIG. 18B).

The combined data with respect to isomerization of the aspartic acid D92 and aggregation indicate that 75 mM $CaCl_2$ is a particularly useful divalent cation concentration for preventing or reducing isomerization and preserving polypeptide bioactivity because only minor levels of polypeptide aggregation resulted at 29° C. Regarding isoaspartic acid, the above results demonstrate that a wide range of $CaCl_2$ concentrations, including within the range of 25-150 mM, significantly slowed aspartic acid isomerization. To further control aggregation or particle formation in divalent salt-containing formulations, surfactants such as polysorbate 20 or 80 can be additionally included.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A formulation comprising a buffer having a pH from about 4.0 to less than 6.0, a divalent cation between about 5-150 mM, an excipient comprising a sugar or polyol and an effective amount of a therapeutic antibody having specific binding activity to human epidermal growth factor receptor (EGFR), wherein said therapeutic antibody retains at least about 80% stability for up to two months in solution, and wherein the divalent cation is at least one of $CaCl_2$, $ZnCl_2$, $MnCl_2$ or $MgCl_2$.

2. The formulation of claim 1, wherein said divalent cation concentration is selected from about 25 mM, 50 mM, 75 mM, 100 mM or 125 mM.

3. The formulation of claim 1, wherein the divalent cation is $CaCl_2$ and is present at a concentration of 75 mM.

4. The formulation of claim 1, wherein said pH is between 4.8-5.2.

5. The formulation of claim 1, wherein said buffer is selected from acetic acid, glutamic acid or succinic acid, or a salt thereof.

6. The formulation of claim 1, wherein said buffer comprises a concentration of about 1-50 mM.

7. The formulation of claim 1, wherein said sugar or polyol is selected from glycerol, sucrose, trehalose or sorbitol.

8. The formulation of claim 7, further comprising about 1-20% glycerol, sucrose, trehalose or sorbitol.

9. The formulation of claim 7, further comprising about 1-3% glycerol.

10. The formulation of claim 1, further comprising a surfactant.

11. The formulation of claim 10, wherein said surfactant comprises a polysorbate.

12. The formulation of claim 10, wherein said surfactant is present at a concentration of about 0.001-0.10% (w/v).

13. The formulation of claim 1, further comprising a second excipient.

14. The formulation of claim 13, wherein said second excipient is selected from a buffer, stabilizer, tonicity agent, bulking agent, surfactant, cryoprotectant, lyoprotectant, antioxidant, metal ion, chelating agent and preservative.

15. The formulation of claim 1, wherein said therapeutic antibody having specific binding activity to human EGFR comprises an Asp or Asn residue susceptible to isomerization to isoaspartic acid.

16. The formulation of claim 1, wherein said therapeutic antibody having specific binding activity to human EGFR is a human antibody, a humanized antibody, a chimeric antibody, or a functional fragment thereof.

17. The formulation of claim 16, wherein said human antibody is panitumumab.

18. The formulation of claim 16, wherein said chimeric antibody is Erbitux® (cetuximab).

19. The formulation of claim 16, wherein said human antibody is selected from IMC-11F8 or HUMAX-EGFR.

20. The formulation of claim 16, wherein said humanized antibody is selected from matuzumab (EMD-7200) or nimotuzumab (TheraCIM hR3).

21. The formulation of claim 16, wherein said functional fragment thereof comprises a Fd, Fv, Fab, F(ab'), $F(ab)_2$, $F(ab')_2$, single chain Fv (scFv) or chimeric antibody.

22. The formulation of claim 1, wherein said therapeutic antibody is present at a concentration selected from between about 10-200 mg/ml.

* * * * *